(12) United States Patent
Yu et al.

(10) Patent No.: US 12,067,882 B2
(45) Date of Patent: Aug. 20, 2024

(54) MOTORCADE REGULATION METHOD, DEVICE, ELECTRONIC EQUIPMENT AND STORAGE MEDIUM

(71) Applicant: SHENZHEN TECHNOLOGY UNIVERSITY, Guangdong (CN)

(72) Inventors: Xinjia Yu, Guangdong (CN); Tao Cheng, Guangdong (CN); Tielin Shi, Guangdong (CN)

(73) Assignee: SHENZHEN TECHNOLOGY UNIVERSITY, Shenzhen (CN)

( * ) Notice: Subject to any disclaimer, the term of this patent is extended or adjusted under 35 U.S.C. 154(b) by 224 days.

(21) Appl. No.: 17/886,936

(22) Filed: Aug. 12, 2022

(65) Prior Publication Data
US 2023/0112972 A1   Apr. 13, 2023

Related U.S. Application Data

(63) Continuation of application No. PCT/CN2021/123148, filed on Oct. 11, 2021.

(51) Int. Cl.
*G08G 1/00* (2006.01)
*G08G 1/052* (2006.01)
(Continued)

(52) U.S. Cl.
CPC ............... *G08G 1/20* (2013.01); *G08G 1/052* (2013.01); *G16B 5/00* (2019.02); *G16B 40/00* (2019.02)

(58) Field of Classification Search
CPC ............ G08G 1/123; G08G 1/20; G08G 1/22; G08G 1/052; G16B 40/00; G16B 40/10;
(Continued)

(56) References Cited

U.S. PATENT DOCUMENTS 9,141,112 B1 * 9/2015 Loo .................. G08G 1/096838
10,948,927 B1 * 3/2021 Harris ..................... H04W 4/42
(Continued)

OTHER PUBLICATIONS

S. Sreenivasamurthy and K. Obraczka, "Towards Biologically Inspired Decentralized Platooning for Autonomous Vehicles," 2021 IEEE 93rd Vehicular Technology Conference (VTC2021—Spring), Helsinki, Finland, 2021 (Year: 2021).*

*Primary Examiner* — Russell Frejd
*Assistant Examiner* — Brandon Z Willis

(57) ABSTRACT

Disclosed are a motorcade regulation method, a device, an electronic equipment and a storage medium. A diffusion region of pheromones is constructed by taking a first vehicle main body determined from a multi-cooperative task as a center; a second pheromone set of a second vehicle main body meeting with the first vehicle main body is perceived by using the first pheromone set generated outwardly by the first vehicle main body based on the neural autocrine mechanism; when the second vehicle main body satisfies a proximity condition and an affinity of the pheromones of the first and second vehicle main bodies satisfies a regulation condition, the second vehicle main body is selected to be regulated, and upon regulation, a formation is arranged according to the movement parameters of the first and second vehicle main bodies which are then moved towards the cluster position based on the arranged formation.

20 Claims, 7 Drawing Sheets

(51) Int. Cl.
*G16B 5/00* (2019.01)
*G16B 40/00* (2019.01)

(58) Field of Classification Search
CPC .......... G16B 5/00; G05D 1/02; G05D 1/0287; G05D 1/0293; G05D 1/0295
See application file for complete search history.

(56) References Cited

U.S. PATENT DOCUMENTS

| | | | |
|---|---|---|---|
| 2020/0057453 A1* | 2/2020 | Laws | G05D 1/0088 |
| 2021/0148716 A1* | 5/2021 | Atanasiu | G06Q 10/047 |
| 2022/0043463 A1* | 2/2022 | Cheng | G05D 1/0295 |

* cited by examiner ated with the present invention, a more accurate output.

MOTORCADE REGULATION METHOD, DEVICE, ELECTRONIC EQUIPMENT AND STORAGE MEDIUM

CROSS REFERENCE TO RELATED APPLICATIONS

The present application is a Continuation Application of PCT Application No. PCT/CN2021/123148 filed on Oct. 11, 2021, the contents of which are incorporated herein by reference in their entirety.

TECHNICAL FIELD

The present invention relates to the technical field of motorcade self-organizing networks, and more particularly, to neural autocrine mechanism based motorcade regulation method, device, electronic equipment, and storage media.

BACKGROUND

With the development of communication technology, especially wireless communication and smart vehicle direction, the internet of vehicles has become the most active branch of the internet of things, gets great interest in the field of intelligent traffic, and now is internationally recognized best means of improving driving safety, improving transportation efficiency and achieving energy saving and emissions reduction.

At present, the vehicle network is mainly used to display the mutual communication between the main bodies in the motorcade in cooperative tasks, to increase the cooperation degree to a certain extent, but there is a significant decrease in cooperation degree when there are multiple tasks in the cooperative task at the same time. For this case, a solution for main body capacity reporting was devised, distributed motion control is carried out for each main body through the reported capacity. However, for the existing main body capacity report, it is mainly autonomously triggered and reported by the main body, and the reported information is not guaranteed to be detailed, which results in the fact that at the time of task allocation or during planning collaboration schemes, there is a low utilization and cooperation degree of the main bodies, and breakthroughs in the ultimate utilization of information such as resources of the main bodies are difficult to achieve.

SUMMARY

The primary object of the present invention is to provide neural autocrine mechanism based motorcade regulation method, device, electronic equipment and storage medium, to solve the technical problem that the existing motorcade regulation solution has low accuracy formation and regulation for the motorcade in multi-cooperative task.

According to a first aspect of the present invention, a neural autocrine mechanism based motorcade regulation method is provided, the motorcade regulation method includes:

determining a cluster position, a target position, and at least one first vehicle main body of a motorcade according to a multi-cooperative task and planning a moving path for each first vehicle main body to move to the cluster position;

constructing a diffusion region of a pheromone of each first vehicle main body by taking each first vehicle main body as a center, and generating a first pheromone set within the diffusion region based on the neural autocrine mechanism, wherein the first pheromone set includes at least one first pheromone;

during a moving process of each first vehicle main body on corresponding moving path thereof towards the cluster position, perceiving in real time, whether a second pheromone set transmitted by a second vehicle main body entering the diffusion region satisfies a preset proximity condition, via the first pheromone set, wherein the second pheromone set includes at least one second pheromone;

when the proximity condition is satisfied, determining an affinity between the first pheromone set and the second pheromone set according to the first pheromone set and the second pheromone set;

determining whether the affinity satisfies a preset regulation condition;

when the regulation condition is satisfied, acquiring a movement parameter of each of the first vehicle main body and the second vehicle main body, arranging a formation for the first vehicle main body and the second vehicle main body according to the movement parameters, with which the first vehicle main body and the second vehicle main body continue to move towards the cluster position; and upon arrival of all of the first vehicle main body and the second vehicle main body at the cluster position, re-arranging the formation for all of the first vehicle main body and the second vehicle main body according to the movement parameters and making the re-arranged formation move towards the target position.

Optionally, determining a cluster position, a target position, and at least one first vehicle main body of a motorcade and planning a moving path for each of the first vehicle main bodies to move to the cluster position, according to a multi-cooperative task includes:

determining whether each first vehicle main body has a pre-cooperative vehicle main body;

when yes, taking the moving path as a filtering condition, and selecting a vehicle main body having a specific position on the moving path from the corresponding pre-cooperative vehicle main bodies, to obtain a pre-cooperative vehicle main body set;

determining a real-time position of the first vehicle main body and calculating an information transmission direction of the first vehicle main body and each pre-cooperative vehicle main body in the corresponding pre-cooperative vehicle main body set based on the real-time position;

taking the first vehicle main body as a transmission starting point and constructing a directional diffusion region of the pheromone of the first vehicle main body in the information transmission direction; and invoking the neural autocrine mechanism to drive the first vehicle main body to produce the first pheromone set within the directional diffusion region, and configuring the first pheromone set to transmit directionally within the directional diffusion region in accordance with the information transmission direction.

Optionally, determining a cluster position, a target position, and at least one first vehicle main body of a motorcade and planning a moving path for each of the first vehicle main bodies to move to the cluster position, according to a multi-cooperative task further includes:

determining a maximum information transmission distance of the first vehicle main body when no pre-cooperative vehicle main body is determined for each first vehicle main body;

taking the maximum information transmission distance as a radius and constructing a surrounding diffusion region of the pheromone of the first vehicle main body; and invoking the neural autocrine mechanism to drive the first vehicle main body to produce the first pheromone set within the surrounding diffusion region, and configuring a transmission direction of the first pheromone set to be omni-directional, to transmit the first pheromone set simultaneously in multiple directions within the surrounding diffusion region.

Optionally, perceiving in real time whether a second pheromone set transmitted by a second vehicle main body entering the diffusion region satisfies a preset proximity condition, via the first pheromone set includes:

perceiving whether a new vehicle main body enters the diffusion region via each first pheromone in the first pheromone set;

when the new vehicle main body enters the diffusion region, acquiring a second pheromone set, a intention and a target, which are transmitted by the new vehicle main body within the diffusion region;

selecting a vehicle main body having the target and the intent the same as the multi-cooperative task, and reading the second pheromone set of the selected vehicle main body, to obtain a second pheromone sequence;

calculating and modifying a pheromone concentration of the second pheromone sequence;

determining whether the modified pheromone concentration of the second pheromone set is greater than the pheromone concentration of the first pheromone set; and when not, determining that the new vehicle main body is the second vehicle main body adjacent to the first vehicle main body.

Optionally, determining an affinity between the first pheromone set and the second pheromone set according to the first pheromone set and the second pheromone set includes:

extracting all informational properties of each pheromone of the first pheromone set and the second pheromone set, respectively;

calculating a corresponding pheromone vector according to all informational properties of each pheromone, to obtain a first pheromone vector and a second pheromone vector; and calculating a similarity between the first pheromone set and the second pheromone set according to the first pheromone vector and the second pheromone vector, to obtain a corresponding affinity.

Optionally, calculating a similarity between the first pheromone set and the second pheromone set according to the first pheromone vector and the second pheromone vector, to obtain a corresponding affinity includes:

performing a square summing for differences between every two corresponding pheromone vectors of two identical or similar pheromones in the first pheromone set and the second pheromone set, to obtain the similarity of the two identical or similar pheromones; and calculating a similarity weight for each of the pheromones according to a weight ratio of each pheromone in the multi-cooperative task, and summing the calculated similarity weights to obtain an affinity between the first pheromone set and the second pheromone set.

Optionally, the movement parameter includes at least a movement speed, a movement acceleration, a movement direction, and a diffusion distance of the pheromone, re-arranging the formation for all of the first vehicle main body and the second vehicle main body according to the movement parameters and making the re-arranged formation move towards the target position includes:

performing a fusion calculation based on the movement speed, the movement acceleration, the movement direction and the diffusion distance, to obtain a dynamic performance of each first vehicle main body and each second vehicle main body;

according to the dynamic performance, arranging all of the first vehicle main body and the second vehicle main body in accordance with a preset formation strategy to obtain a cooperative formation;

creating a motorcade self-regulating feedback mechanism based on the cooperative formation, wherein the motorcade self-regulating feedback mechanism is used to monitor a dynamic balance of all movement parameters of each first vehicle main body and each second vehicle main body in the cooperative formation; and controlling all of the first vehicle main body and the second vehicle main body, maintaining a moving queue in accordance with the cooperative formation, and making real-time monitoring adjustment to each vehicle main body in the queue with the motorcade self-regulating feedback mechanism, to achieve movement to the target location, wherein the real-time monitoring adjustment includes: capturing a real-time dynamic performance of the first vehicle main body or the second vehicle main body in the cooperative formation based on the motorcade self-regulating feedback mechanism, determining whether the real-time dynamic performance satisfies a balance coefficient of the cooperative formation, and when not, controlling the corresponding vehicle main body to adjust the dynamic performance thereof, and notifying the other vehicle main body to make a cooperation adjustment.

According to a second aspect of the present invention, a neural autocrine mechanism based motorcade regulation device is provided, the motorcade regulation device includes:

an information collecting module, configured to determine a cluster position, a target position, and at least one first vehicle main body of a motorcade according to a multi-cooperative task and plan a moving path for each first vehicle main body to move to the cluster position;

a constructing module, configured to construct a diffusion region of a pheromone of each first vehicle main body by taking each first vehicle main body as a center, and generate a first pheromone set within the diffusion region based on the neural autocrine mechanism, wherein the first pheromone set includes at least one first pheromone;

a perceiving module, configured to, during a moving process of each first vehicle main body on corresponding moving path thereof towards the cluster position, perceive in real time whether a second pheromone set transmitted by a second vehicle main body entering the diffusion region satisfies a preset proximity condition, via the first pheromone set, wherein the second pheromone set includes at least one second pheromone;

an affinity calculating module, configured to determine an affinity between the first pheromone set and the second pheromone set according to the first pheromone set and the second pheromone set when the second vehicle main body satisfying the proximity condition is perceived;

a determining module, configured to determine whether the affinity satisfies a preset regulation condition; and a regulation module, configured to, upon determining that the regulation condition is satisfied, acquire a movement parameter of each of the first vehicle main body and the second vehicle main body, arrange a formation for the first vehicle main body and the second vehicle main body according to the movement parameters, with which the first vehicle main body and the second vehicle main body continue to move towards the cluster position; and upon arrival of all of the first vehicle main body and the second vehicle main body at the cluster position, re-arrange the formation for all of the first vehicle main body and the second vehicle main body according to the movement parameters and make the re-arranged formation move towards the target position.

Optionally, the constructing module includes:

a first determining unit, configured to determine whether each first vehicle main body has a pre-cooperative vehicle main body;

a selecting unit, configured to take the moving path as a filtering condition, and select a vehicle main body having a specific position on the moving path from the corresponding pre-cooperative vehicle main bodies, when there is the pre-cooperative vehicle main body is determined, to obtain a pre-cooperative vehicle main body set;

a first calculating unit, configured to determine a real-time position of the first vehicle main body and calculate an information transmission direction of the first vehicle main body and each pre-cooperative vehicle main body in the corresponding pre-cooperative vehicle main body set based on the real-time position a first constructing unit, configured to take the first vehicle main body as a transmission starting point and construct a directional diffusion region of the pheromone of the first vehicle main body in the information transmission direction; and a first diffusing unit, configured to invoke the neural autocrine mechanism to drive the first vehicle main body to produce the first pheromone set within the directional diffusion region, and configure the first pheromone set to transmit directionally within the directional diffusion region in accordance with the information transmission direction.

Optionally, the constructing module further includes:

a distance determining unit, configured to determine a maximum information transmission distance of the first vehicle main body when no pre-cooperative vehicle main body is determined for each first vehicle main body;

a second constructing unit, configured to take the maximum information transmission distance as a radius and construct a surrounding diffusion region of the pheromone of the first vehicle main body; and a second diffusing unit, configured to invoke the neural autocrine mechanism to drive the first vehicle main body to produce the first pheromone set within the surrounding diffusion region, and configure a transmission direction of the first pheromone set to be omni-directional, to transmit the first pheromone set simultaneously in multiple directions within the surrounding diffusion region.

Optionally, the perceiving module includes:

a perceiving unit, configured to perceive whether a new vehicle main body enters the diffusion region via each first pheromone in the first pheromone set;

an acquiring unit, configured to, when the new vehicle main body enters the diffusion region, acquire a second pheromone set, a intention and a target, which are transmitted by the new vehicle main body within the diffusion region;

a reading unit, configured to select a vehicle main body having the target and the intent the same as the multi-cooperative task, and read the second pheromone set of the selected vehicle main body, to obtain a second pheromone sequence;

a second calculating unit, configured to calculate and modifying a pheromone concentration of the second pheromone sequence;

a second determining unit, configured to determine whether the modified pheromone concentration of the second pheromone set is greater than the pheromone concentration of the first pheromone set; and a concentration determining unit, configured to determine that the new vehicle main body is the second vehicle main body adjacent to the first vehicle main body upon determining that the modified pheromone concentration of the second pheromone set is not greater than the pheromone concentration of the first pheromone set.

Optionally, the affinity calculating module includes:

an extracting unit, configured to extract all informational properties of each pheromone of the first pheromone set and the second pheromone set, respectively;

a vector calculating unit, configured to calculate a corresponding pheromone vector according to all informational properties of each pheromone, to obtain a first pheromone vector and a second pheromone vector; and an affinity calculating unit, configured to calculate a similarity between the first pheromone set and the second pheromone set according to the first pheromone vector and the second pheromone vector, to obtain a corresponding affinity.

Optionally, the affinity calculation unit is configured to:

perform a square summing for differences between every two corresponding pheromone vectors of two identical or similar pheromones in the first pheromone set and the second pheromone set, to obtain the similarity of the two identical or similar pheromones; and calculate a similarity weight for each of the pheromones according to a weight ratio of each pheromone in the multi-cooperative task, and sum the calculated similarity weights to obtain an affinity between the first pheromone set and the second pheromone set.

Optionally, the movement parameter includes at least a movement speed, a movement acceleration, a movement direction, and a diffusion distance of the pheromone, and the regulating module includes:

a fusion unit, configured to perform a fusion calculation based on the movement speed, the movement acceleration, the movement direction and the diffusion distance, to obtain a dynamic performance of each first vehicle main body and each second vehicle main body;

an arranging unit, configured to according to the dynamic performance, arrange all of the first vehicle main body and the second vehicle main body in accordance with a preset formation strategy to obtain a cooperative formation;

a creating unit, configured to create a motorcade self-regulating feedback mechanism based on the cooperative formation, wherein the motorcade self-regulating feedback mechanism is used to monitor a dynamic balance of all movement parameters of each first vehicle main body and each second vehicle main body in the cooperative formation; and a regulating unit, configured to control all of the first vehicle main body and the second vehicle main body, maintain a moving queue in accordance with the cooperative formation, and make real-time monitoring adjustment to each vehicle main body in the queue with the motorcade self-regulating feedback mechanism, to achieve movement to the target location, wherein the real-time monitoring adjustment includes: capturing a real-time dynamic performance of the first vehicle main body or the second vehicle main body in the cooperative formation based on the motorcade self-regulating feedback mechanism, determining whether the real-time dynamic performance satisfies a balance coefficient of the cooperative formation, and when not, controlling the corresponding vehicle main body to adjust the dynamic performance thereof, and notifying the other vehicle main body to make a cooperation adjustment.

A third aspect of the present invention provides an electronic equipment, which includes: a memory, a processor, and a computer program stored in the memory and executable on the processor, wherein when executed by the processor, the computer program implements the steps of the neural autocrine mechanism based motorcade regulation method according to the first aspect described above.

A fourth aspect of the present invention provides a computer readable storage medium storing a computer program, when executed by a processor, the computer program implements the steps of the neural autocrine mechanism based motorcade regulation method according to the first aspect described above.

Benefits:

In the technical solution of the present invention, a diffusion region of pheromones is constructed by taking a first vehicle main body determined from a multi-cooperative task as a center; a second pheromone set of a second vehicle main body meeting with the first vehicle main body is perceived by using the first pheromone set generated outwardly by the first vehicle main body based on the neural autocrine mechanism; when the second vehicle main body satisfies a proximity condition and an affinity of the pheromones of the first vehicle main body and the second vehicle main body satisfies a regulation condition, the second vehicle main body is selected to be regulated, and upon regulation, a formation is arranged according to the movement parameters of the first vehicle main body and the second vehicle main body, and the first vehicle main body and the second vehicle main body are moved towards the cluster position based on the arranged formation. Vehicles satisfying the regulation conditions are selected by fully utilizing the capabilities of the vehicle main bodies when the motorcade is regulated, and formation and regulation among multiple vehicle main bodies in multi-cooperative tasks are realized, so that the transportation capabilities of each vehicle main body are fully arranged, and the transportation efficiency and the regulation accuracy are improved.

DESCRIPTION OF THE EMBODIMENTS

Figure 1:
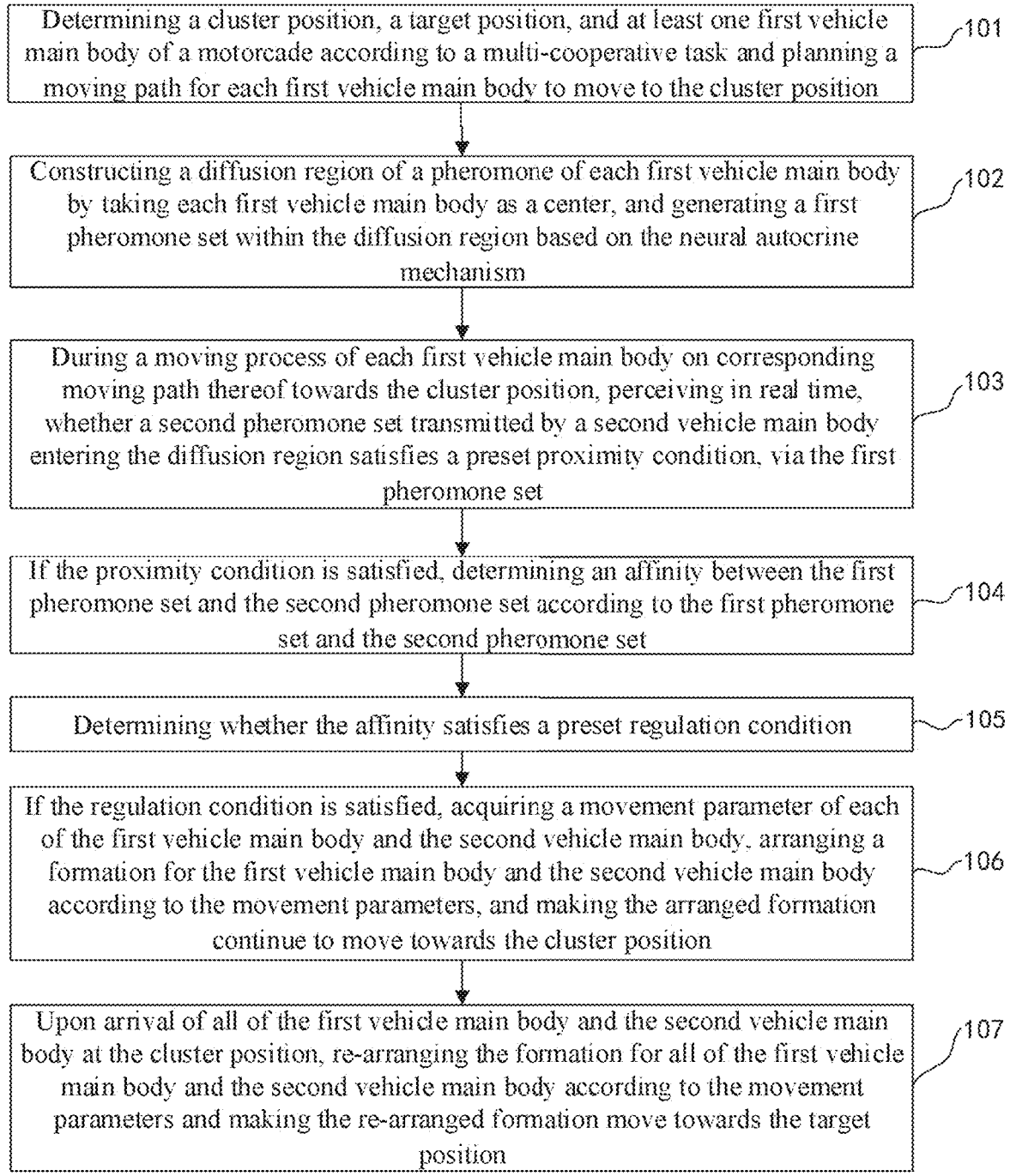
FIG. 1 is a schematic illustration of a first embodiment of a neural autocrine mechanism based motorcade regulation method provided by the present invention.

With respect to the problems existing in motorcade regulation schemes, a neural autocrine mechanism based motorcade regulation method is proposed. This scheme is mainly aimed at the process of how do a plurality of vehicle main bodies spontaneously and autonomously dynamically form an interest body based on their inherent intention and interest target respectively, in the absence of third-party external force driving or centralized control, so as to jointly obtain opportunities, cooperate and work cooperatively to complete the multi-cooperative task, a specific implementation is realized in the following two ways:

One is that, a preliminary association can be established, through directional transmission of pheromones carrying various information to several friend Agents (of which physical address and/or network address is known) of the vehicle main body Agent through communication network for the purpose of exchanging information with each other; and the pheromones of several Agents that have established association are transmitted and diffused to more Agents in the same manner through the friends of the friend Agents, so as to realize an agglomeration of multiple Agents;

The other is that, a pheromone can be perceived and relevant information thereof can be obtained by other Agents through an Agent's homogeneity and uniform release and diffusion of pheromones to the surrounding, and the perceiving Agent will further migrate to the perceived Agent to ensure that its pheromones can be perceived by the perceived Agent, so as to realize the association of the relationship between the two Agent.

Further, a combination, a comparison and an affinity/similarity calculation of pheromone sequences (composed of several pheromone fragments) of each two Agents of several Agents that have established preliminary association and agglomeration are carried out, to eliminate Agents with large differences in various aspects and keep several Agents with close similarities, for self-organized formation of a dynamic alliance or dynamic system with a common target; the dynamic system will operate according to its own mechanisms and methods of self-organization, negotiation, risk sharing, benefit sharing, resource sharing, division of labor and collaboration, collaborative work, operation control and self-regulation, to achieve goals thereof, thereby addressing the technical problem of existing motorcade regulation schemes having less precision in formation and regulation for motorcade in a multi-cooperative task.

The terms "first", "second", "third", "fourth", and the like, if any, in the description and in the claims of the present invention and in the appended drawings, are used to distinguish similar objects and not necessarily for describing a particular sequential or sequential order. It is to be understood that data so used may be interchanged under appropriate circumstances such that the embodiments described herein are capable of being practiced in other sequences than illustrated or described herein. Furthermore, the terms "include" or "have" and any variation thereof, are intended to cover non-exclusive inclusion, for example, a process, method, system, product or apparatus that comprises a list of steps or elements is not necessarily limited to those steps or elements expressly listed, but may include other steps or elements not expressly listed or inherent to such process, method, product or apparatus.

For ease of understanding, a specific flow of an embodiment of the invention is described below, referring to FIG. 1, a first embodiment of a neural autocrine mechanism based motorcade regulation method in accordance with embodiments of the present invention includes:

101. determining a cluster position, a target position, and at least one first vehicle main body of a motorcade according to a multi-cooperative task and planning a moving path for each first vehicle main body to move to the cluster position;

In this embodiment, After the multi-cooperative task is determined, a target location specified in the multi-cooperative task and the region where the task is located are extracted, a two-dimensional planar space is constructed based on the region, and a coordinate value of the target location in the two-dimensional planar space is calculated, where the two-dimensional planar space can be described as a planar space composed of two elements of length (X axis) and width (Y axis), with four quadrants. Each point on the plane is represented by a coordinate value (x, y) or a polar coordinate value (p, γ), where $$\rho = \sqrt{x^2 + y^2}, \gamma = \tan^{-1}\frac{y}{x}.$$

Further, the vehicle main bodies available in the region where the task is located are screened, in particular the available vehicle main bodies are determined based on a cargo in the multi-cooperative task, and may also be determined by directly screening the states of the vehicle main bodies, after the determination, at least one first vehicle main body from the available vehicle main bodies is further screened out. In practical applications, this application selects more than two vehicle main bodies and other available vehicle main bodies are used as the vehicle main bodies to be matched in the subsequent planned path, a second vehicle main body is matched from these vehicle main bodies.

Whereas for extraction of the cluster position, the location specified in the task may be directly taken as the cluster position, it is also possible to take a calculated compromise point based on the filtered first vehicle main bodies as the cluster position. However, no matter which one is selected, the first vehicle main bodies need to arrive at the cluster position for the processing of the task. In turn, it is necessary to plan the moving path for each first vehicle main body to move to the cluster position. When the path is planned, the specific plan is planned based on the principle of seeking the cooperation of other vehicle main bodies, that is, all available vehicle main bodies screened are used as a path planning pool to plan a path on which most vehicle main bodies can be encountered, so as to form the final moving path. In practical applications, obstacles within the region need to be taken into account when the moving path is planned.

In practical applications, the first vehicle main body to be selected is preferably chosen in a randomly generated manner, vehicle main bodies Agents having different capabilities (functions, performances), resources, working status (busy/idle/malfunctioning, etc.), motion status (speed, acceleration, etc.), willingness/intent and objectives, and being independent of each other, and mutually equal, are chosen.

102. constructing a diffusion region of a pheromone of each first vehicle main body by taking each first vehicle main body as a center, and generating a first pheromone set within the diffusion region based on the neural autocrine mechanism, wherein the first pheromone set comprises at least one first pheromone;

In this step, the diffusion region to be constructed is specifically constructed based on the ability of each first vehicle main body. The distance of the diffusion region of each first vehicle main body is not necessarily the same. The standard is specifically set based on the furthest communication distance of the first vehicle main body.

In practical applications, the information transmission direction of the diffusion region of each first vehicle main body is set as omnidirectional, such that the capability of the first vehicle main body to be perceived by other vehicle main bodies is improved, and the capability of the first vehicle main body perceiving other vehicle main bodies is also improved.

In this embodiment, after the diffusion region is constructed, the first vehicle main body is controlled according to the neural autocrine mechanism to produce pheromones, the pheromones refer to the vehicle main body's individual element and its associated properties (values), cooperative element and its associated properties (values), task and state element and its associated properties (values), and resource capability (including price) element and its associated properties (values), and so on.

In this embodiment, in addition to construction of the diffusion region for the first vehicle main body, it is also necessary to build the diffusion region and pheromones for all available vehicle main bodies in the region where the task is located.

103. during a moving process of each first vehicle main body on corresponding moving path thereof towards the cluster position, perceiving in real time, whether a second pheromone set transmitted by a second vehicle main body entering the diffusion region satisfies a preset proximity condition, via the first pheromone set, wherein the second pheromone set includes at least one second pheromone;

In this step, after all vehicle main bodies' diffusion regions and pheromones have been constructed, each first vehicle main body is controlled to move towards the cluster position according to the moving path, during the moving procedure, the above steps is executed in real time, to keep the diffusion region of the first vehicle main body unchanged, and the pheromones are transmitted through the diffusion region by using the neural autocrine mechanism in real time, the transmitted pheromone is used to sense in real time whether there is a vehicle main body within a certain range of the position where the first vehicle main body passes through, when yes, the perceived vehicle main body will be used as an alternative second vehicle main body.

In practical applications, upon perception of the vehicle main body, all pheromones of the first vehicle main body are used to perceive a concentration of the pheromones of the perceived vehicle main body. Specifically, the concentration of the pheromones of the perceived vehicle main body is determined by the following perception calculation equation:

$$Sen_i(t, P_k(t)) = \begin{cases} P_{ik}(t) \geq \tau_k P_{TV}^k, \text{ then } A_k \text{ is near } A_i \\ \text{else } A_k \text{ is not near } A_i \end{cases},$$

Where $P_{ik}$ represents the pheromone concentration of $A_k$ perceived by $A_i$, $\tau_k$ is a correction factor of (0, 1), $P^k_{TV}$ is a minimum concentration value released by $A_k$ that can be perceived by other vehicle main body, and the information on a pheromone segment carried by $P^k_{TV}$ is not lost.

104. when the proximity condition is satisfied, determining an affinity between the first pheromone set and the second pheromone set according to the first pheromone set and the second pheromone set;

In this step, the affinity can be understood as a similarity, as in capturing, perceiving and determining the presence of other vehicle main bodies in vicinity, it needs combination, matching, comparison and affinity calculations of pheromones of the both vehicle main bodies, to exclude vehicle main bodies with willingness, intention and target inconsistencies, behavior state conflicts, or big difference in other aspect as potential collaborators, which can be calculated with simply L2 norm Euclidean distance.

In practical applications, each vehicle main body produces a plurality of pheromones based on the neural autocrine mechanism, and each pheromone carries various information, however when the affinity (i.e. similarity) is calculated, first a vector composed of various information carried in each pheromone is calculated, a difference value between that pheromone and a corresponding similar or identical pheromone is calculated based on the vector, and the similarity of the two pheromones is obtained based on the difference value, the first vehicle main body $\text{Agent}_i(A_i)$ and the second vehicle main body $\text{Agent}_k(A_k)$ are taken as examples.

In the following, the first vehicle main body $\text{Agen}(A_i)$ includes $ipA^i_1$, $ipA^i_2$, ..., $ipA^i_{n_1}$, with corresponding pheromone vectors $\overrightarrow{ipAttr_i} = (ipA^i_1, ipA^i_2, \ldots, ipA^i_{n_1})$. The second vehicle main body Age $(A_k)$ includes $ipA^k_1$, $ipA^2_k$, ..., $ipA^k_{n_1}$, with corresponding pheromone vectors $\overrightarrow{ipAttr_k} = (ipA^k_1, ipA^k_2, \ldots, ipA^k_{n_1})$. The similarity of a first pheromone in the first pheromone set and a second pheromone in the second pheromone set are calculated from the two pheromone vectors, thereby obtaining an affinity of the two pheromones, the equation is as follows:

$$S(\overrightarrow{ipAttr_i}, \overrightarrow{ipAttr_k}) = \sqrt{\sum^{n_1}_u |ipA^i_u - ipA^k_u|^2}$$

105. Determining whether the affinity satisfies a preset regulation condition;

Specifically, when whether the affinity satisfies the regulation condition is determined, when the first pheromone set and the second pheromone set each has a plurality of pheromones, prior to determination of whether the affinity satisfies the condition, a weight ratio of each pheromone is further determined, a weight ratio of the similarity of each pheromone is determined based on the weight ratio, a combined similarity of the two pheromone sets is calculated based on the weight ratios, i.e. an overall similarity, the equation is $S(A_i, A_k) = \omega_1 * S(\overrightarrow{ipAttr_i}, \overrightarrow{ipAttr_k})$.

106. when the regulation condition is satisfied, acquiring a movement parameter of each of the first vehicle main body and the second vehicle main body, arranging a formation for the first vehicle main body and the second vehicle main body according to the movement parameters, with which the first vehicle main body and the second vehicle main body continue to move towards the cluster position;

In this embodiment, the movement parameter includes at least a movement speed, a movement acceleration, a movement direction, and a diffusion distance of the pheromone. Upon formation of the first vehicle main body and the second vehicle main body in accordance with the movement parameters, firstly a target movement direction of the formation is determined, the movement direction ends in particular with the cluster position, shortest distances between center positions of the first vehicle main body and the second vehicle main body and the cluster position are calculated, in the connecting line with the shortest distance, the direction towards the cluster position is the target movement direction. A moving direction of each of the first vehicle main body and the second vehicle main body is adjusted based on the target movement direction. The first vehicle main body and the second vehicle main body are ranked based on a combined analysis of the movement speed, the movement acceleration, and the diffusion distance, to obtain a formation based on which a movement control is performed.

In practical applications, the formation was arranged according to descending order of pheromone concentration, since $R_v > R_u > R_w$, where R represents the furthest distance the pheromone spreads, it means that that vehicle main body produces the highest pheromone concentration, then make $V_v(t) > V_u(t) > V_w(t)$, to ensure that $A_v$, $A_u$, $A_w$ sequentially reach a rendezvous point and form an formation. However, a mutual safety distance $1.5R_w \leq R_{SD} \leq 2R_w$ has to be guaranteed, where $R_{SD}$ presents the safety distance between two vehicle main bodies, such that distances between all vehicle main bodies forming the formation are not too large (which may causes that the vehicle main bodies in the formation are not able to perceive in time the vehicle main body producing the least concentration of pheromone, such as $A_w$), information of each other can be transmitted and exchanged by diffusion of pheromones to vicinity, to ensure an orderly run of the entire formation in the direction towards the cluster position.

107. upon arrival of all of the first vehicle main body and the second vehicle main body at the cluster position, re-arranging the formation for all of the first vehicle main body and the second vehicle main body according to the movement parameters and making the re-arranged formation move towards the target position.

In this embodiment, after all of the first vehicle main body and the second vehicle main body move to the cluster position according to the formation described in the step 106, a movement parameter of each first vehicle main body is detected, whether the movement parameters satisfy a condition of maintaining the formation is determined, when not, a real-time movement parameter of each of the first vehicle main body and the second vehicle main body is acquired when they arrive at the cluster position, the formation of each of the first vehicle main body and the second vehicle main body is readjusted based on the real-time movement parameter, the adjusted formation moves towards the target position.

In practical applications, the adjustment of the respective first vehicle main body and second vehicle main body is in particular based on speed, speed variation, acceleration, direction and diffusion distance. Preferably, the adjustment herein is to adjust the movement parameters without adjustment to the position or arrangement of each first vehicle main body and second vehicle main body in the overall formation, and the movement parameters are adjusted in accordance with a vehicle main body formation holding mechanism based on an endocrine system autocrine mechanism.

Further, a control amount can also be generated by calculating a difference between the previous movement parameter and the subsequent movement parameter, an adjustment is achieved based on the control amount. Specifically, a ratio, an integral, and a derivative of the deviation of the movement parameter before and after reaching the cluster position are calculated to constitute the control amount through linear combination, to control the controlled object and correct the deviation thereof, to achieve a stable linear, negative feedback closed loop regulator, the linear, negative feedback closed loop regulator achieves the adjustment by monitoring each of the first vehicle main body and the second vehicle main body in real time In embodiments of the invention, after determination of the cluster position, the target position, and the first vehicle main body according to the multi-cooperative task, a diffusion region of pheromones is constructed by taking the first vehicle main body as a center, and the first pheromone set produced by the first vehicle main body is used to perceive a second pheromone set of the second vehicle main body with which the first vehicle main body meets. When the second vehicle main body satisfies the proximity condition and the affinity of pheromones of the both satisfies the regulation condition, then the second vehicle main body is selected for regulation. Upon regulation, the formation is arranged in accordance with movement parameters of the first vehicle main body and the second vehicle main body, the first vehicle main body and the second vehicle main body are controlled to move towards the target position based on the arranged formation. That is, the vehicle main bodies are associated with each other, depending on whether the respective intended targets are consistent or close to those of other vehicle main bodies, whether their own resources, dynamic capabilities, and work status match a cooperation request made by a counterparty (the higher the affinity, the greater the likelihood of cooperation), and whether benefit thus obtained is in accordance with its own expectation, whether to establish a partnership is determined, thereby spontaneously and autonomously forming an interest body. By implementation of such a method, interest ensembles/systems/leagues can be dynamically created or members can be dynamically added and subtracted or dissolved, to flexibly and quickly response to the variety, fast variability and high uncertainty and complexity of external environments, based on the decentralized and autonomous control mechanism of each main body, the self-organization, robustness and reliability of the system are higher than those of the centralized control system.

Figure 2:
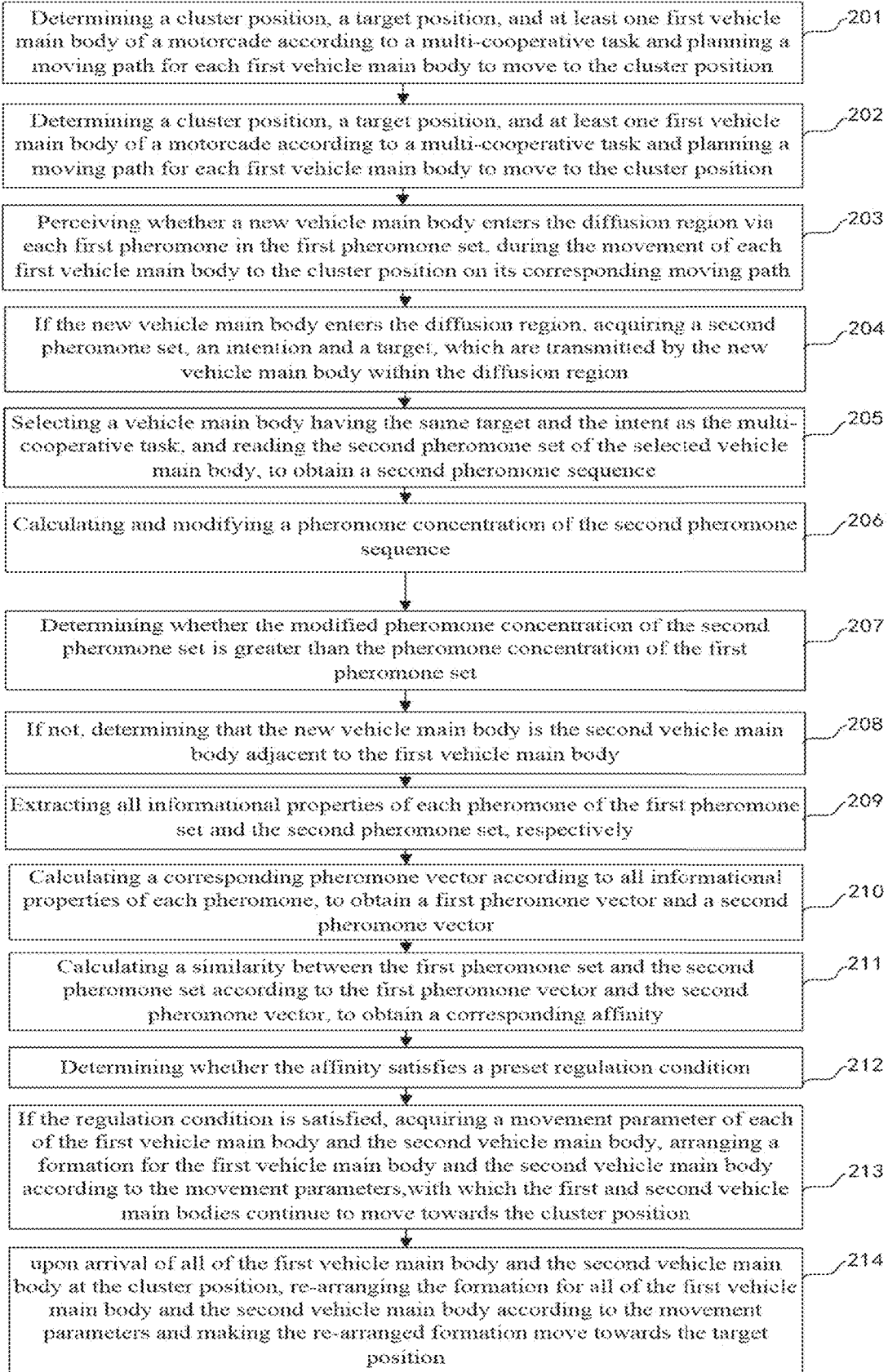
FIG. 2 is a schematic illustration of a second embodiment of a neural autocrine mechanism based motorcade regulation method provided by the present invention.

Referring now to FIG. 2, a second embodiment of the neural autocrine mechanism based motorcade regulation method in the embodiments of the present invention includes:

201. determining a cluster position, a target position, and at least one first vehicle main body of a motorcade according to a multi-cooperative task and planning a moving path for each first vehicle main body to move to the cluster position;

In this step, the cluster position and the target position are specifically extracted directly from a request of the multi-cooperative task, and the at least one first vehicle main body is determined from all available vehicle main bodies within a task region of the multi-cooperative task, and then a portion of all available vehicle main bodies are randomly selected as the first vehicle main body. The first vehicle main body here refers to a triggering body for executing a seeking for cooperation to complete the multi-cooperative task, that is to say that all available vehicle main bodies in the region where the task is located are the first vehicle main bodies, for ease of explanation of the overall process only, the triggering body for executing the seeking for cooperation to complete the multi-cooperative task is referred to as the first vehicle main body, while the vehicle main body selected by the first vehicle main body in the seeking process is referred to as the second vehicle main body.

In practical applications, the first vehicle main body and available vehicle main bodies mentioned above can be achieved by the following steps:

1) building a two-dimensional space;

The two-dimensional space here is specifically constructed based on a geographic location of the multi-cooperative task, and a two-dimensional planar space can be described as a planar space composed of two elements in length (X axis) and width (Y axis), with 4 quadrants. Each point on the planar space is represented by a coordinate value (x, y) or a polar coordinate value (ρ, γ), where $$\rho = \sqrt{x^2 + y^2}, \gamma = \tan^{-1}\frac{y}{x},$$

that is, each vehicle main body can be represented as (x, y) or (ρ, γ).

Figure 3:
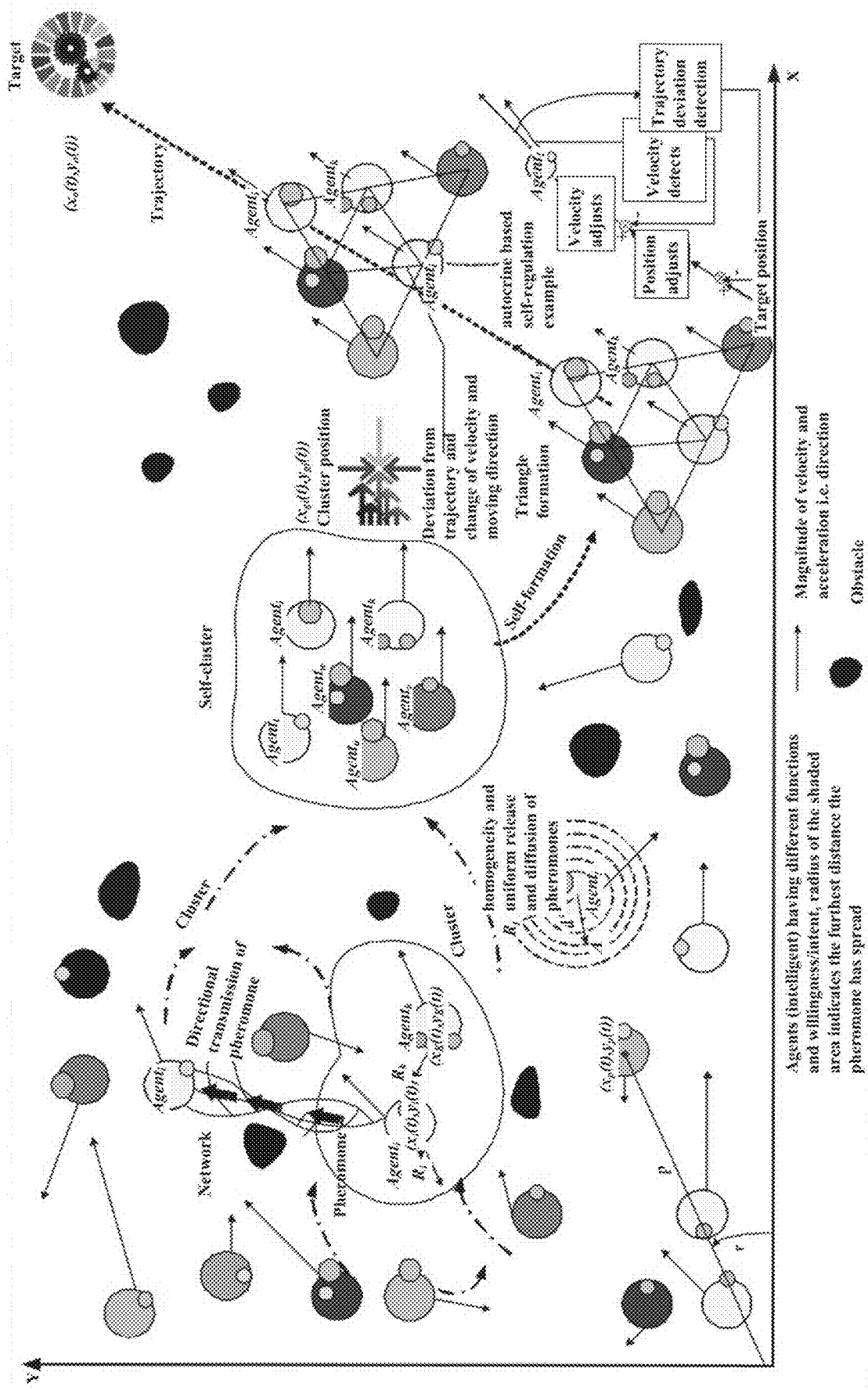
FIG. 3 is a schematic illustration of a principle and a basic idea of the neural autocrine mechanism provided by the present invention.

2) determining an obstacle, and the cluster position and the target position;

In practical applications, in addition to extraction of the vehicle main body, all obstacles of the vehicle main body during movement are further extracted. As shown in FIG. 3, the two-dimensional planar space with 4 quadrants is constructed with X and Y axes, the vehicle main body and obstacles are set one after the other on the two-dimensional planar space. As shown in the figure, there are m' known static obstacles and m" randomly generated obstacles in the two-dimensional plane, the obstacles are represented by $B_w(x(t), y(t))$; the cluster position and the target position may be represented as Gi (x(t), y(t)) and O(x(t), y(t)), respectively.

3) randomly selecting a plurality of vehicle main bodies;

After all available vehicle main bodies in the multi-cooperative task are searched out, a group of vehicle main bodies Agents (see several vehicle main bodies in the left area of FIG. 3) with different capabilities (functions, performances), resources, work status (busy/idle/malfunctioning, etc.), motion status (speed, acceleration, etc.), willingness/intents and goals, and independent of each other, equal to each other, are randomly selected, description can be as follow:

Agent$_i$=A$_i$::=<{x(t), y(t), $\vec{v}$, $\vec{a}$, MD(t), G(t), P(t), Sen(t), S(t)}, i=0, n, x(t), y(t)) presents the position of A$_i$, $\vec{v}$, $\vec{a}$, MD(t), G(t), P(t), Sen(t), S(t) respectively present speed, acceleration, direction, willingness target, pheromone (sequence) concentration, perceptron and state;

The speed and the acceleration of vehicle main body Agent$_i$(A$_i$) can be calculated as $$|v(t)| = \frac{\sqrt{\Delta y(t + \Delta t)^2 + \Delta x(t + \Delta t)^2}}{\Delta t}, a(t) = \frac{\overrightarrow{\Delta v(t + \Delta t)}}{\Delta t};$$

a direction MD (t) is expressed by an angle between itself and the positive direction of the X axis, $$\theta = \tan^{-1}\frac{\left|\vec{v}(y)\right|}{\left|\vec{v}(y)\right|} \left(\vec{v}(y) \text{ and } \vec{v}(x)\right.$$

are projections of the speed vector on Y and X axes, respectively);

The target $G_i(t)$ of $A_i$ may be set as $S(t)::=<\{0,1,2,3,4,5,6,7,8,9,10,\ldots N\}>$, Where 0, 1, 2, 3, 4, 5, 6, 7, 8, 9, 10, ... N may correspond to the serial number of different targets, respectively. For example, the primary target of an intelligent AGV in automated warehousing or unmanned supermarket or unmanned quay, may be assumed as "to make a multi-cooperative motorcade to carry more and/or larger/heavier acquisitions", "to transport cooperatively with some friend AGV thereof", "take a cooperative strategy to cooperate with a friend AGV", "pick up a certain shipment alone", "how many shipments to handle", "which path does it wish to run along," "how much can it profit to handle a certain shipment once", "how to complete the pickup of shipments at different storage locations in one pass as much as possible", "where does it dock", "when will it be maintained", "how to navigate around obstacles", etc. Each Agent's willingness, intent and target can also be described in natural language in the form of string. When multiple Agents self-organize into a dynamic system (such as a motorcade of different formations), to accomplish a task. Through semantic recognition and matching of the intents and targets between each other, vehicle main bodies with the same or similar targets can gather together.

4) Calculating the pheromone concentration $P_i(t)$ released by $A_i$, which can simply be calculated as:

$$P_i(t) = \sum_{i=0}^{n'} \omega_i PS_i \qquad \text{equation (5.5.1)}$$

$$= \sum_{j=0}^{n_1} \omega_j ipAttr_j^i(t) + \sum_{k=0}^{n_2} \omega_k ccpAttr_k^i(t) + \sum_{p=0}^{n_3} \omega_p tspAttr_p^i(t)$$

$$+ \sum_{q=0}^{n_4} \omega_q rcpAttr_q^i(t),$$

Where $PS_i$ represents a pheromone sequence released by $A_i$; $ipAttr_j^i(t)$, $ccpAttr_k^i(t)$, $\omega_p tspAttr_p^i(t)$ and $\omega_q rcpAttr_q^i(t)$ respectively represent its individual element and its associated properties (values), cooperative element and its associated properties (values), task and state element and its associated properties (values), and resource capability (including price) element and its associated properties (values), these properties values need to be normalized; $\Sigma^{n_1}_{j=0}\omega_j=1$, $\Sigma^{n_2}_{j=0}\omega_k=1$, $\Sigma^{n_3}_{p=0}\omega_p=1$, $\Sigma^{n_4}_{q=0}\omega_q=1$;

5) $Sen_i(t)$ presents a perceptron of $A_i$ which enables $A_i$ to perceive and measure the pheromone concentration of other main bodies around $A_i$, to determine whether there are other (intelligent) main bodies around $A_i$, for example, $A_i$ perceives the pheromone concentration $P_{ik}(t)$ of $Agent_k(A_k)$ through its perceptron to determine whether $A_k$ is around $A_i$, which is noted as $Sen_i(t, P_k(t))$ and can be calculated as follows:

(equation 5.5.2)

$$Sen_i(t, P_k(t)) = \begin{cases} P_{ik}(t) \geq \tau_k P_{TV}^k, \text{ then } A_k \text{ is around } A_i \\ \text{else } A_k \text{ is not around } A_i \end{cases}, P_{ik}$$

represents the pheromone concentration of $A_k$ perceived by $A_i$, $\tau_k$ is a correction factor of (0, 1), $P^k_{TV}$ is a minimum concentration value released by $A_k$ that can be perceived by other vehicle main bodies, and the information on a pheromone segment carried by $p^k_{TV}$ is not lost;

$S_i(t)::=<\{-1,0,1,2\}>$, Where −1, 0, 1, 2 present failure, stop working, working, idle and available for work, respectively.

202. constructing a diffusion region of a pheromone of each first vehicle main body by taking each first vehicle main body as a center, and generating a first pheromone set within the diffusion region based on the neural autocrine mechanism;

In this embodiment, the construction for the diffusion region can be implemented in two ways. One is directional construction, the other is omnidirectional construction. That is, the orientation is constructed by selecting one direction from 360 degrees, and an omni-direction includes in all directions. In particular, the construction mode can be chosen according to actual requirements. Firstly it needs to determine whether the first vehicle main body has a determined cooperative vehicle main body. Based on a result of the determination, the following ways may be selected: first, a preliminary association can be established through directional transmission of pheromones carrying various information to several friend Agents of vehicle main body Agent (known physical address and/or network address) through communication network for the purpose of exchanging information with each other; second, by isotropically, uniformly releasing and diffusing pheromones to the surrounding, the Agent can be perceived by other Agents and relevant information thereof is obtain by other Agents, and the perceiving Agent will further migrate to the perceived Agent to ensure that its pheromones can be perceived by the perceived Agent, so as to realize the association of the relationship between the two Agent, thereby thus building a diffusion region.

In this embodiment, the step are embodied as:

determining whether each first vehicle main body has a pre-cooperative vehicle main body;

when it is determined that each first vehicle main body has the pre-cooperative vehicle main body, taking the moving path as a filtering condition, and selecting a vehicle main body having a specific position on the moving path from the corresponding pre-cooperative vehicle main bodies, to obtain a pre-cooperative vehicle main body set; determining a real-time position of the first vehicle main body and calculating an information transmission direction of the first vehicle main body and each pre-cooperative vehicle main body in the corresponding pre-cooperative vehicle main body set based on the real-time position; taking the first vehicle main body as a transmission starting point and constructing a directional diffusion region of the pheromone of the first vehicle main body in the information transmission direction; and invoking the neural autocrine mechanism to drive the first vehicle main body to produce the first pheromone set within the directional diffusion region, and configuring the first pheromone set to transmit directionally within the directional diffusion region in accordance with the information transmission direction;

when no pre-cooperative vehicle main body is determined for each first vehicle main body, determining a maximum information transmission distance of the first vehicle main body according to each first vehicle main body; taking the maximum information transmission distance as a radius and constructing a surrounding diffusion region of the pheromone of the first vehicle main body; and invoking the neural autocrine mechanism to drive the first vehicle main body to produce the first pheromone set within the surrounding diffusion region, and configuring a transmission direction of the first pheromone set to be omni-directional, to transmit the first pheromone set simultaneously in multiple directions within the surrounding diffusion region.

In practical applications, the vehicle main body in the environment or system can produce pheromones according to their own intent, willingness, target, environmental stress and stimuli. To maximize and possibly achieve their own goal of interest, survival and development, it is necessary in most cases by generating, releasing most basic relevant information required for cooperation which includes, but not limited to, individual element, cooperative element, task and state element, and resource capability element.

The diffusion of each vehicle main body can occur in two ways:

First, when the particular address, location of the cooperative main body can be determined, the pheromone can be directed by using a communication network (see $Agent_i$ and $Agent_1$ in FIG. 3), or by means of environmental diffusion in the case of no network or no cooperative main body nearby;

Second, without knowing, nor determining, the location of any main body, the vehicle main body can then isotropically release the pheromones to their surroundings by taking itself as the center (see $Agent_j$ in FIG. 3), the pheromone concentration is greatest at the center (noted $P^j_{max}(t)$), the farther away from the center and the lower the concentration, the less likely it is to be perceived by other vehicle main bodies, in this case, the pheromone concentration at each diffusion point can be calculated as follows:

$$P_j(t, d^j_A) = \mu \frac{P^j_{max}(t) * e^{-t/r}}{(\pi R_j)^2 * d^j_A}, \quad \text{(equation 5.5.3)}$$

Where $P_j(t, d^j_A)$ represents the pheromone concentration at a point at a distance d (noted $d^j_A$) from the center of $A_j$, $\mu$ is a correction factor of (0, 1), $R_j$ is the farthest distance the pheromone diffuses (i.e. Where the pheromone concentration is 0), and r is an average lifetime of the pheromones.

203. Perceiving whether a new vehicle main body enters the diffusion region via each first pheromone in the first pheromone set, during the movement of each first vehicle main body to the cluster position on its corresponding moving path;

On the basis of the pheromone transmission and diffusion regime as described above in step 202, each vehicle main body in the environment constantly captures, perceives and measures pheromones released by other Agents by using its respective perceptron and the equation 5.5.2, to determine whether there are other vehicle main bodies nearby (which may be neighbors in physical location, friends with friendly cooperation or close relationship, or neighbors in network address).

204. when the new vehicle main body enters the diffusion region, acquiring a second pheromone set, an intention and a target, which are transmitted by the new vehicle main body within the diffusion region;

In particular, when the perceived pheromone concentration of the vehicle main body satisfies $P_{ik}(t) \geq \tau_k P^k_{TV}$, the entry of the new vehicle main body is determined, and a second pheromone released by the new vehicle main body is collected via the perceptron (i.e. each pheromone), to obtain a second pheromone set.

205. Selecting a vehicle main body having the same target and the intent as the multi-cooperative task, and reading the second pheromone set of the selected vehicle main body, to obtain a second pheromone sequence;

206. Calculating and modifying a pheromone concentration of the second pheromone sequence;

207. Determining whether the modified pheromone concentration of the second pheromone set is greater than the pheromone concentration of the first pheromone set;

208. when not, determining that the new vehicle main body is the second vehicle main body adjacent to the first vehicle main body;

In this embodiment, in particular, whether there is the entry of the new vehicle main body is determined by determining whether the vehicle main body is an adjacent main body of the first vehicle main body. That is to say, the entry here should meet the requirement of being the adjacent main body. Specifically, it is judged by perceiving the pheromone concentration of an approaching vehicle main body, of which the realization process is as follow:

the first vehicle main body uses its own perceptron to perceive the surrounding vehicle main body or the vehicle main body in a known pheromone transmission direction, and perceives the pheromone concentration of the vehicle main body, wherein the pheromone concentration releasing by each vehicle main body can be identified as:

$$P_i(t) = \sum_{i=0}^{n'} \omega_i PS_i =$$

$$\sum_{j=0}^{n_1} \omega_j ipAttr^i_j(t) + \sum_{k=0}^{n_2} \omega_k ccpAttr^i_k(t) + \sum_{p=0}^{n_3} \omega_p tspAttr^i_p(t) + \sum_{q=0}^{n_4} \omega_q rcpAttr^i_q(t)$$

Where $PS_i$ represents the pheromone sequence released by $A_i$; $ipAttr^i_j(t)$, $ccpAtt^i_k(t)$, $\omega_p tspAttr^i_p(t)$ and $\omega_q rcpAttr^i_q(t)$ represent the individual element and its associated properties (values), cooperative element and its associated properties (values), task and state element and its associated properties (values), and resource capability (including price) element and its associated properties (values), respectively.

When the first vehicle main body $A_i$ perceives the pheromone concentration $P_{ik}(t)$ of each vehicle main body $Agent_k$ ($A_k$) through its perceptron to determine whether $A_k$ is around $A_i$, it can be denoted as $Sen_i(t, P_k(t))$ and can be calculated as follow:

$$Sen_i(t, P_k(t)) = \begin{cases} P_{ik}(t) \geq \tau_k P^k_{TV}, A_k \text{ is around } A_i \\ \text{else } A_k \text{ is not } A_i \end{cases} \quad \text{(equation 5.5.2)}$$

Where $P_{ik}$ represents the pheromone concentration of $A_k$ perceived by $A_i$, $\tau_k$ is the correction factor of (0, 1), $P^k_{TV}$ is the minimum concentration value released by $A_k$ that can be perceived by other main body, and the information on the pheromone segment carried by $P^k_{TV}$ is not lost;

$S_i(t) ::= <\{-1,0,1,2\}>$, where $-1$, 0, 1, 2 present failure, stop working, working, idle and available for work, respectively.

209. extracting all informational properties of each pheromone of the first pheromone set and the second pheromone set, respectively;

210. Calculating a corresponding pheromone vector according to all informational properties of each pheromone, to obtain a first pheromone vector and a second pheromone vector;

211. Calculating a similarity between the first pheromone set and the second pheromone set according to the first pheromone vector and the second pheromone vector, to obtain a corresponding affinity;

This step specifically includes: performing a square summing for differences between every two corresponding pheromone vectors of two identical or similar pheromones in the first pheromone set and the second pheromone set, to obtain the similarity of the two identical or similar pheromones; and calculating a similarity weight for each of the pheromones according to a weight ratio of each pheromone in the multi-cooperative task, and summing the calculated similarity weights to obtain an affinity between the first pheromone set and the second pheromone set.

In practical applications, as in capturing, perceiving and determining the presence of other vehicle main bodies in vicinity, it needs combination, matching, comparison and affinity calculations of pheromones of the both main bodies, to exclude vehicle main bodies with willingness, intention and target inconsistencies, behavior state conflicts, or big difference in other aspect as potential collaborators, which can be calculated with simply L2 norm Euclidean distance. The vehicle main body $Agent_i$ ($A_i$) and the vehicle main body $Agent_k$ ($A_k$) are taken as example for illustration:

1) The pheromone of $A_i$ is a sequence of pheromones composed of primary pheromones (segments) such as individual element, cooperative element, task and state element, and resource capability element and so on, and each pheromone (segment) carries a variety of information and is expressed by different information properties. Each pheromone segment can thus be seen as a vector composed of multiple information properties, the vector is shown as follow:

$$\overrightarrow{ipAttr_i} = (ipA^i_1, ipA^i_2, \ldots, ipA^i_{n_1}), \overrightarrow{ccpAttr_i} = (ccpA^i_1, ccpA^i_2, \ldots, ccpA^i_{n_2}),$$

$$\overrightarrow{tspAttr_i} = (tspA^i_1, tspA^i_2, \ldots, tspA^i_{n_3}),$$

$$\overrightarrow{rcpAttr_i} = (rcpA^i_1, rcpA^i_2, \ldots, rcpA^i_{n_4});$$

2) Likewise, for the pheromone sequence of $Agent_k(A_k)$, its vector is as follows:

$$\overrightarrow{ipAttr_k} = (ipA^k_1, ipA^k_2, \ldots, ipA^k_{n_1}),$$

$$\overrightarrow{ccpAttr_k} = (ccpA^k_1, ccpA^k_2, \ldots, ccpA^k_{n_2}),$$

$$\overrightarrow{tspAttr_k} = (tspA^k_1, tspA^k_2, \ldots, tspA^k_{n_3}),$$

$$\overrightarrow{rcpAttr_k} = (rcpA^k_1, rcpA^k_2, \ldots, rcpA^k_{n_4});$$

3) The similarity (affinity) between the corresponding vectors is separately calculated:

$$S(\overrightarrow{ipAttr_i}, \overrightarrow{ipAttr_k}) = \sqrt{\sum_u^{n_1} |ipA^i_u - ipA^k_u|^2}$$

$$S(\overrightarrow{ccpAttr_i}, \overrightarrow{ccpAttr_k}) = \sqrt{\sum_u^{n_2} |ccpA^i_u - ccpA^k_u|^2}$$

$$S(\overrightarrow{tspAttr_i}, \overrightarrow{tspAttr_k}) = \sqrt{\sum_u^{n_3} |tspA^i_u - tspA^k_u|^2}$$

$$S(\overrightarrow{rcpAttr_i}, \overrightarrow{rcpAttr_k}) = \sqrt{\sum_u^{n_4} |rcpA^i_u - rcpA^k_u|^2}$$

Each element of the above pheromone (segment) vector needs to be normalized.

4) The total similarity of main body $Agent_i$ ($A_i$) and main body $Agent_k$ ($A_k$) may be calculated as:

$$S(A_i, A_k) = \omega_1 * S(\overrightarrow{ipAttr_i}, \overrightarrow{ipAttr_k}) + \omega_1 * S(\overrightarrow{ccpAttr_i}, \overrightarrow{ccpAttr_k}) + \omega_1 * S(\overrightarrow{tspAttr_i}, \overrightarrow{tspAttr_k}) + \omega_1 * S(\overrightarrow{rcpAttr_i}, \overrightarrow{rcpAttr_k}),$$

where $\Sigma^4_{i=1} \omega_i = 1$, and the magnitude of a weight coefficient may be determined by determining strategies such as importance, dominant role, etc. of individual element, cooperative element, task and state element, and resource capability element based on requirement for actual collaboration.

212. determining whether the affinity satisfies a preset regulation condition;

213. when the regulation condition is satisfied, acquiring a movement parameter of each of the first vehicle main body and the second vehicle main body, arranging a formation for the first vehicle main body and the second vehicle main body according to the movement parameters, and with which the first vehicle main body and the second vehicle main body continue to move towards the cluster position;

In this step, when the regulation conditions are not satisfied, the steps of 201-212 are repeated, and relevant property values and parameters of N vehicle main bodies are calculated. In particular the pheromone concentration of each vehicle main body Agent is calculated, several Agents next to $A_i$ at time instant t are perceptually calculated and found, and the similarity (affinity) of pheromones of each two Agents is calculated, according to steps 206-211.

Taking FIG. 3 as an example, it is finally found that pheromones of $Agent_i$ ($A_i$), $Agent_k$ ($A_k$), $Agent_1$ ($A_1$), $Agent_u$ ($A_u$), $Agent_v$ ($A_v$), $Agent_w$ ($A_w$), etc. are highly similar and less different and can be logically organized together to form an initial formation group, which lays the foundation for the next formation arranging.

214. upon arrival of all of the first vehicle main body and the second vehicle main body at the cluster position, re-arranging the formation for all of the first vehicle main body and the second vehicle main body according to the movement parameters and making the re-arranged formation move towards the target position.

In this embodiment, the movement parameter includes at least a movement speed, a movement acceleration, a movement direction, and a diffusion distance of the pheromone, and the formation is embodied as:

Performing a fusion calculation based on the movement speed, the movement acceleration, the movement direction and the diffusion distance, to obtain a dynamic performance of each first vehicle main body and each second vehicle main body;

According to the dynamic performance, arranging all of the first vehicle main body and the second vehicle main body in accordance with a preset formation strategy to obtain a cooperative formation;

Creating a motorcade self-regulating feedback mechanism based on the cooperative formation, wherein the motorcade self-regulating feedback mechanism is used to monitor a dynamic balance of all movement parameters of each first vehicle main body and each second vehicle main body in the cooperative formation; and Controlling all of the first vehicle main body and the second vehicle main body, maintaining a moving queue in accordance with the cooperative formation, and making real-time monitoring adjustment to each vehicle main body in the queue with the motorcade self-regulating feedback mechanism, to achieve movement to the target location, wherein the real-time monitoring adjustment comprises: capturing a real-time dynamic performance of the first vehicle main body or the second vehicle main body in the cooperative formation based on the motorcade self-regulating feedback mechanism, determining whether the real-time dynamic performance satisfies a balance coefficient of the cooperative formation, and when not, controlling the corresponding vehicle main body to adjust the dynamic performance thereof, and notifying the other vehicle main body to make a cooperation adjustment.

In practical applications, during movement of the first vehicle main body towards the cluster position, there are two ways for seeking cooperative vehicle main bodies. first is that, there is no clear target object or destination in the environment or system, then there is an alignment of the movement speed and direction of each Agent in the initial formation queue on that of the Agent with the highest pheromone concentration (such as in Agent$_i$ in FIG. 3), and a value of a safe distance to the preceding Agent that needs to be maintained is calculated and adjusted according to this speed; sub-steps 4)-5) of step 201, and steps 202-213 are repeated to aggregate more Agent to join the formation until a limit number is reached; since there is no target direction of movement, the group of Agents, upon achievement of formation according to the method described above in a designated assembling place, then select a movement direction with a certain probability to try to find the target; the target is also constantly releasing pheromones to draw the formation closer; this is repeated until the formation finds the target and moves to the target position; movement and trajectory deviations occurring in certain Agents can also be self-adjusted according to the first case described above, to maintain the entire formation.

Another is that there is an explicit target object and address thereof in the environment or system, the movement speed and direction of each Agent are moving towards the target position $(x_o(t), y_o(t))$; during movement, sub-steps 4) to 5) of step 201, steps 202-213 are repeated to find and aggregate more Agents with similar and/or close pheromones to stepwise join the formation one after another until a limit number is reached; a position for cluster and formation $(x_{gi}(t), y_{gi}(t)$ is designated, the Agent closest to the target object is arranged at the head of the formation (such as the triangle formation), and the rest Agent can be arranged in the similar manner; then the speed of the Agent with the largest pheromone concentration is used as the speed of all Agents, and a value of a safe distance to the preceding Agent that needs to be maintained is calculated and adjusted according to this speed; during movement, some Agents may fluctuate in speed, position (motion trajectory) resulting in deviations, this requires that each Agent shall has the ability of self-adaptive adjustment of speed and position (see Agent$_1$ in FIG. 3), and has a full closed loop regulation system with negative feedback of speed and position, which is composed of a speed ring (inner ring) and a position ring (outer ring), to constantly perceive its own speed and position (trajectory) and make according adjustment. A regulation controller can be a fuzzy controller or an adaptive PID controller, or an intelligent controller optimized based on neuroendocrine immune regulation. In this way, it can ensure that each Agent runs at a prescribed speed, trajectory until reaching the position of the target object.

Figure 4:
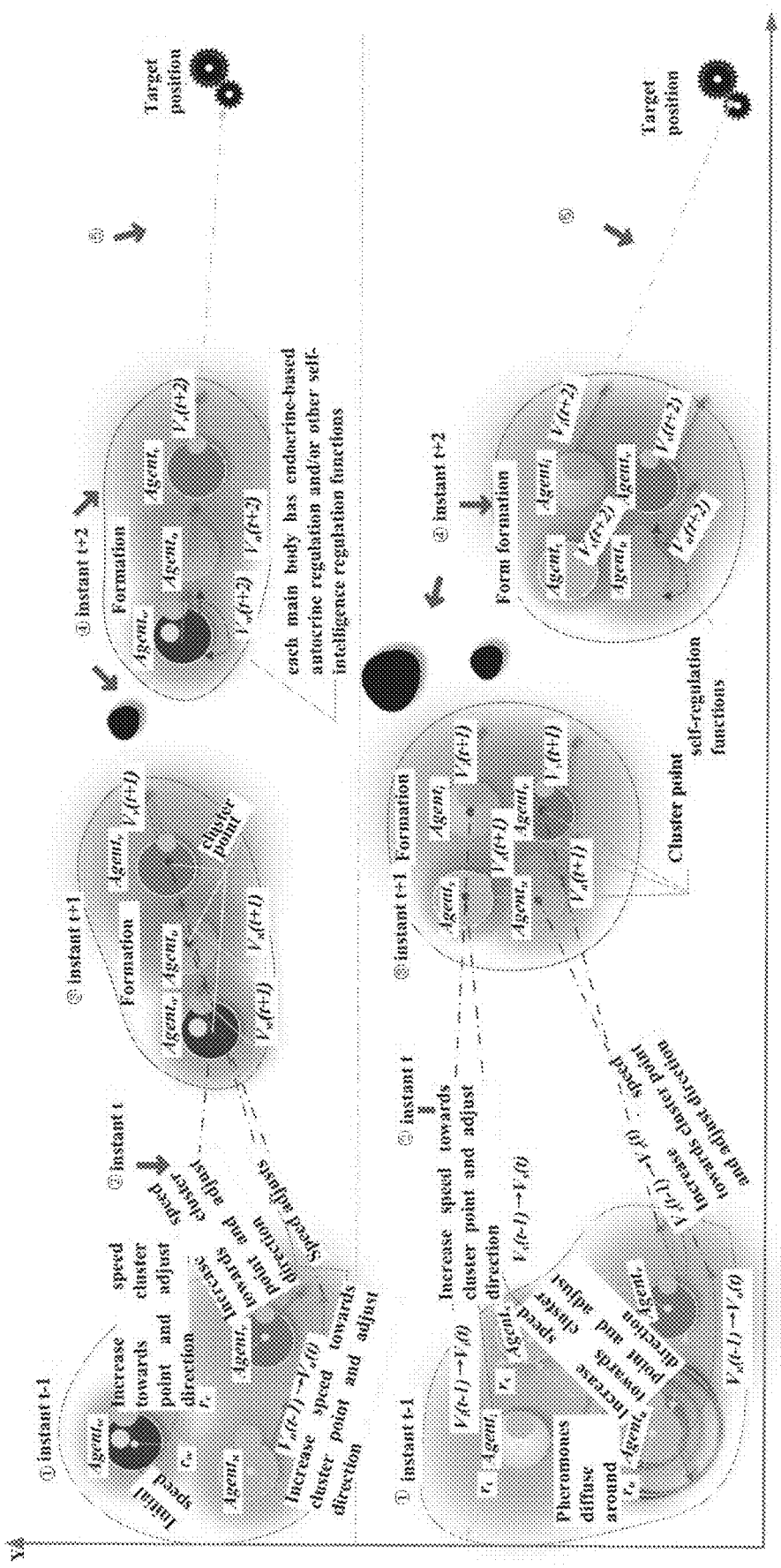
FIG. 4 is a schematic illustration of a linear formation and a square formation of vehicles provided by the preset invention

In this embodiment, the formation comprises a linear formation and a square formation. For the linear formation, the vehicle main bodies clustered together can be arranged in a low or a column in accordance with a certain order, regardless of the number of vehicle main bodies is an even number or an odd number. As shown in FIG. 4, the formation process is as follows:

①At instant t−1, three Agentss Agent$_v$(A$_v$), Agent$_u$(A$_u$), Agent$_w$(A$_w$) realize mutual perception and combination through pheromone transmission or diffusion;

②At instant t, the formation was arranged according to descending order of pheromone concentration, since $R_v > R_u > R_w$, (R represents the furthest distance the pheromone spreads, and it also means that the main body produces the highest pheromone concentration), then $V_v(t) > V_u(t) > V_w(t)$, to ensure that A$_v$, A$_u$, A$_w$ sequentially reach a rendezvous point and form an formation. However, a mutual safety distance $1.5R_w \leq R_{SD} \leq 2R_w$ has to be guaranteed (where RSD represents a safe distance between two vehicle main bodies), such that distances between all vehicle main bodies forming the formation are not too large (which may causes that the vehicle main bodies in the formation are able to perceive in time the vehicle main body producing the least concentration of pheromone, such as A$_w$), information of each other can be transmitted and exchanged by diffusion of pheromones to vicinity, to ensure an orderly run of the entire formation;

③At instant t+1, Agent$_v$, Agent$_u$ and Agent$_w$ forms a linear formation one after another, move at the same speed $V_v(t+1)$, $V_u(t+1)$, $V_w(t+1)$, and keep a safe distance $R_{SD}$ from each other;

④At instant t+2, the leading main body A$_v$ can perceive an obstacle, the entire formation must adjust the speed to navigate around the obstacle and move towards the target position;

⑤At every moment since the formation was formed, each main body is able to sense the speed and position of itself and other main bodies (it is possible to obtain a global formation rather than local information through dispersion of pheromones and transmission of information to each other between adjacent main bodies, which is essential for motion planning, adaptive regulation, coordination and cooperation of each main body and formation group). When there is a deviation from the overall speed and the track of the formation or a deviation from the safety distance between each other, adjustments are made based on respective self-regulation mechanisms to ensure the formation, the safety, and overall arrival at the target position.

For a square formation, all main bodies are arranged into an m×n matrix in a certain order, and m≠n or n×n. As shown in FIG. 4, the formation process is as follows:

At instant t−1, pheromones of four Agents Agent$_i$(A$_i$), Agent$_v$(A$_v$), Agent$_u$(A$_u$), Agent$_s$(A$_s$) are transmitted (For example, although A$_u$ and A$_s$ are far apart, they are friends of each other, they can directionally transfer and exchange their pheromones through a communication network) or diffused (the other main bodies every two are close by each other and can be mutually perceived through pheromone diffusion to aggregate together), thereby achieving mutual perception and integration;

②At instant t, firstly the type of the formation is determined based on the number of the main bodies clustered together, when the number is even, the formation can be formed according to m×n or n×n, and the formation can be formed row by row according to the sequence number of the pheromone concentration from large to small; A$_i$, A$_v$, A$_u$ and A$_s$ may be arranged in a 2×2 formation. Since $R_{vi} > R_v > R_u > R_s$, then $V_i(t) > V_v(t) > V_u(t) > V_s(t)$ should be set to ensure that A$_i$, A$_v$, A$_u$, and A$_s$ sequentially reach a cluster point respectively and forms the formation at the same time, safe distances between every two main bodies per row and between every two main bodies per column should be guaranteed that $1.5R_s \leq R_{SD} \leq 2R_s$;

③ at instant t+1, the 2×2 formation $$\begin{Vmatrix} A_i & A_v \\ A_u & A_s \end{Vmatrix}$$

is formed and every main bodies move at the same speed $V_i(t-1)$, $V_v(t-1)$, $V_u(t-1)$ and $V_s(t-1)$, and each main body maintains a safe distance $R_{SD}$ from the main bodies in the surrounding;

④ at instant t+2, the leading main bodies $A_i$ and $A_v$ can perceive the encounter of 2 obstacles, the entire formation must adjust speed to bypass the obstacles and move towards the target position;

⑤ is the same as ⑤ of the "linear formation", and will not be repeated.

A triangle formation, i.e. all main bodies form different triangle formations (isosceles right triangle, equilateral triangle, etc.) in a certain order. It should be emphasized that each main body in the triangular formation must be kept at a safety distance $1.5R_{min} \leq R_{SD} \leq 2R_{min}$ from the main bodies surrounding it, to ensure that every two main bodies can transfer information through the pheromones in time, so that the global information can be obtained in time to prevent collisions and maintain formation uniformity and symmetry among the main bodies during movement; moreover, each main body has endocrine-based autocrine regulation and/or other self-intelligence regulation functions.

In practical applications, the motorcade self-regulating feedback mechanism is specifically a vehicle main body formation maintaining mechanism based on an autocrine mechanism of endocrine system. Autocrine is an important function that an endocrine system in the body autonomously adjusts (inhibits, excites or regulates) physiological functions and activity states of cells. The so-called autocrine is the regulation of function and activity level on itself. Some endocrine cells firstly secrete the hormones (or regulatory peptides) they produce into their own external tissue fluids, then use hormone receptors on their own surface to combine with these hormones/regulatory peptides, to make themselves produce chemical biological reactions, to achieve the purpose of self-regulation. In this process, the hormone or regulatory peptide itself doesn't participate in the regulatory process, acts only as a messenger. With this simple yet efficient regulation mechanism, functions, behaviors, activity states, etc. of the vehicle main body individual in a MAS-based intelligent system can be self-regulated, to response changes in their surroundings. For example, this mechanism can be applied to multiple vehicle main bodies in a disordered state, how do they move and gather, how do they reach the cluster position and form an formation, and how do they change a movement state to regulate speed and position thereof when speed, trajectory (position) deviation arises to themselves or when encountering obstacles throughout the formation motion.

Each Agent in the formation has the ability of obtaining the speed, position and related information carried by other pheromone of all other Agents in the formation, i.e. has the ability of obtaining global information. All Agents in the formation can move with the speed of the Agent with the largest pheromone concentration (which can also be calculated and adjusted in magnitude and direction based on methods such as artificial potential field method according to the distances from itself to the target and the obstacle) towards the target position.

Each intelligent main body Agent is able to perceive changes of its own speed and position. Take $Agent_u$ (Au) in FIG. 4 as an example to illustrate its self-perception of its speed and direction changes in every interval $\Delta t$:

At instant t+2, position, speed and direction of $A_u$ are respectively $(x(t+2), y(t+2))$, $v_u(t+2)$, $\theta_u(t+2)$, and at instant $t+2+\Delta t$, the position is $(x(t+2+\Delta t), y(t+2+\Delta t))$, then its speed, change of speed, acceleration and direction are respectively $$v_u(t+2+\Delta t) = \frac{\sqrt{(x(t+2+\Delta t)^2 + y(t+2+\Delta t))^2} - \sqrt{(x(t+2)^2 + y(t+2))^2}}{\Delta t}$$

then the change of speed is $\Delta v_u = v_u(t+2+\Delta t) - v_u(t+2)$, the acceleration is $$a(t) = \frac{\overrightarrow{\Delta v_u}}{\Delta t}, \theta_u(t+2) = \tan^{-1}\left|\frac{\overrightarrow{v_{u(t+2)}}(y)}{\overrightarrow{v_{u(t+2)}}(x)}\right| = \tan^{-1}\frac{y_o - y_u(t+2)}{x_o - x_u(t+2)}, (x_o, y_o)$$

is the position coordinates of the target;

At instant $t+2+\Delta t$, the direction of $A_u$ is $MD(t+2+\Delta t)$, and is presented by the angle between itself and the positive axis $$\theta_u(t+2+\Delta t) = \tan^{-1}\left|\frac{\overrightarrow{\Delta v_u(t+2+\Delta t)}(y)}{\overrightarrow{\Delta v_u(t+2+\Delta t)}(x)}\right| (\overrightarrow{\Delta v_u(t+2+\Delta t)}(y) \text{ and } \overrightarrow{\Delta v_u(t+2+\Delta t)}(x))$$

and
are the projections of the velocity vector on the Y-axis and the X-axis respectively), then, the deviation direction of $A_u$ is $\Delta \theta_u = \theta_u(t+2+\Delta t) - \theta_u(t+2)$;

When $|\Delta \theta_u| > 0$ and/or $|\Delta v_u| > 0$, it presents that the velocity and moving direction of $Agent_u$ change, which triggers the $Agent_u$ produce self-regulating hormones $P^c_u(t+2+\Delta t) \in (0,1)$ that act on $Agent_u$, such that $\Delta v_u \to 0$ and $\Delta \theta_u \to 0$. To maintain the stability of the Agent, during regulation, the speed and direction are adjusted according to the following equations:

$$v_u(t+2+2\Delta t) = v_u(t+2+\Delta t) - k_v * \Delta v_u$$

$$\theta_u(t+2+2\Delta t) = \theta_u(t+2+\Delta t) - k_\theta * \Delta \theta_u$$

Where a velocity adjustment coefficient is $k_v \in (0,1)$ and a direction adjustment coefficient is $k_\theta \in (0,1)$, a calculation is as follow:

$$P^c_u(t+2+\Delta t) = \alpha * P^c_u(t+2) + \beta * e^{-\frac{t}{r}} + \gamma * \left(\frac{1/2}{1+e^{-(|\Delta v_u|)}} + \frac{1/2}{1+e^{-|\Delta \theta_u|}}\right),$$

An adjustment coefficient of self-regulating hormone at a previous time is $\alpha \in (0,1)$, an adjustment coefficient for calculating attenuation is $\beta \in (0,1)$, r is the lifetime of the hormone, $\gamma$ is an adjustment coefficient related to velocity and direction change, and $r > \alpha$ and $r > \beta$. When $P^c_u(t+2+\Delta t) \geq m$ (m is a threshold of the self-regulating hormone), when the self-regulating hormone plays a stimulant role, then $k_v \in (0.5,1)$ and $k_\theta \in (0.5,1)$, else play an inhibiting role, then $k_v \in (0,0.5)$ and $k_\theta \in (0,0.5)$.

Figure 5:
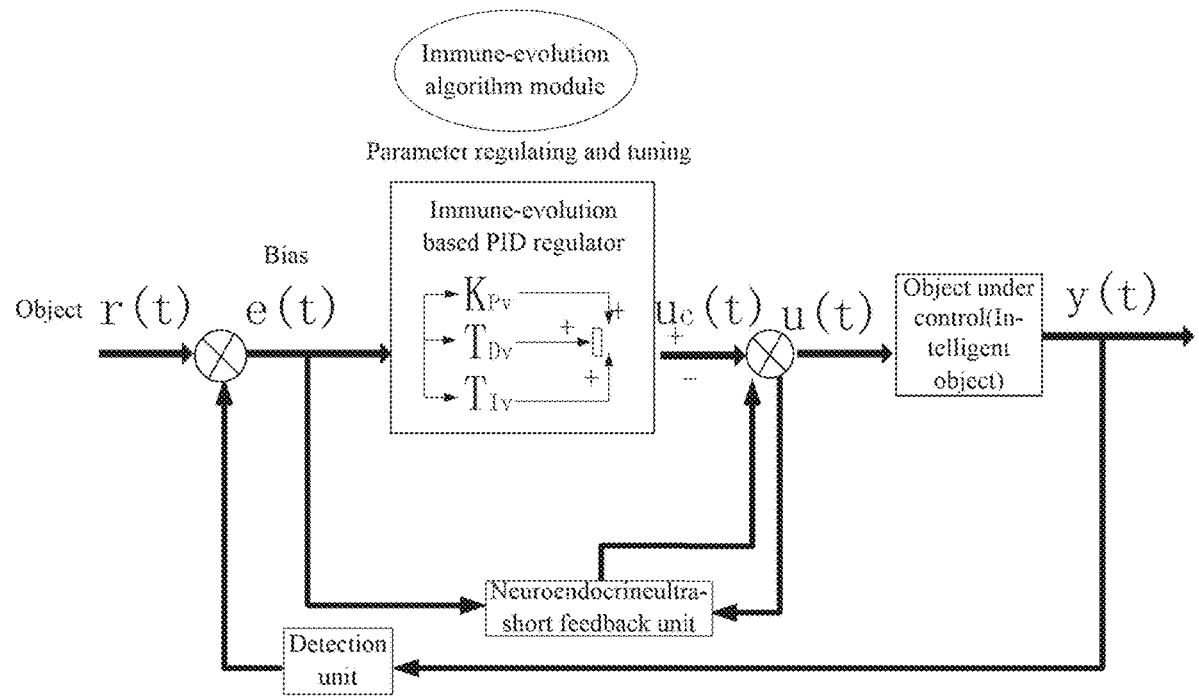
FIG. 5 is a schematic illustration of a principle of a motorcade self-regulating feedback mechanism provided by the present invention.

In this embodiment, the motorcade self-regulating feedback mechanism may also be a novel type of intelligent PID control system based on neuroendocrine immune-regulating mechanism, as shown in FIG. 5, includes mainly an immune-evolution based PID regulator, an immune-evolution algorithm module, an ultra-short feedback unit, an detection unit, object under control, and so on. In this control system, r(t) is a system desired input, y(t) is a system actual output, e(t) is a dynamic control bias generated by the system due to perturbations, u(t) is an output of an immune-evolution based PID controller; $K_p$ is a proportionality coefficient of PID, which is sensitive to bias e(t) and effective to reduce bias; $K_i$ is an integral coefficient, having functions of eliminating static differences, maintaining system stability and memory; $K_d$ is a differential coefficient that can represent the current trend of deviation change and reduce system adjustment time.

For a PID control algorithm, the PID control is essentially a linear, negative feedback closed loop regulator that combines the proportional, integral and derivative of the deviation into a control quantity through a linear combination to control the object under control to correct its deviation to bring it to a steady state. The PID controller has been a classic well-established control method widely used in industrial automation for decades due to its simple structure, good stability, reliable operation, easy operation and convenient adjustment. The differential equation for the PID controller is as follows:

$$u(t) = K_p\left[e(t) + \frac{1}{T_i}\int_0^t e(t)dt + T_d\frac{de(t)}{dt}\right], \text{ and } e(t) = r(t) - y(t);$$

The difference equation for digital PID controller (position control type) is $$u(n) = K_p\left\{e(n) + \frac{T_s}{T_i}\sum_{k=0}^n e(n) + \frac{T_d}{T_s}[e(n) - e(n-1)]\right\} + u_0,$$

$T_s$ is a sampling period.

In order to meet the practical needs of different application fields and further improve the performance of PID control, based on the standard PID controller, it is improved in terms of adaptive adjustment, tuning and optimization of the adjustment parameters, incomplete and complete differential and differential first and then filter, anti-integration saturation (integral limit, integral separation, variable speed integration), elimination of integral insensitivity zones, reasonable selection and optimization of sampling periods, etc. There are many related research efforts and practical applications which will not be repeated here.

For the immune-evolution algorithm, a PID parameter regulating and tuning method based on the immune-evolution algorithm is provided on the basis of the PID regulator. Although the PID controller has many advantages mentioned above, its function and performance depend entirely on the selection, determination and optimization of its proportional, integral and derivative coefficients, which is also complex and requires many factors for proper regulation and setting, and is extremely critical and important. In general, adjustments and optimizations of PID-related parameters may be considered in terms of interrelationships between parameters, effect mechanism of parameters on system dynamic and steady state performance, first proportion and then integral and differential, conservative settings at the beginning of parameter values, response times, overshoots, adjustment times, trade-offs between perturbation resistance and steady-state error, and the like. In recent years, intelligent methods such as expert systems, genetic algorithms, flora algorithms, immunological algorithms, fuzzy logic, neural networks, machine learning, neuroendocrine regulation, colony algorithms, and the like are applied, crossed and derived in PID controller and its parameter tuning, to achieve intelligence of the PID control and most control effect on the object under control and also further expand application scope thereof.

Given the advantages of immune algorithms generated by borrowing and mimicking the human immune system and its regulatory mechanisms in terms of self-organization, self-learning and memory capabilities, adaptability, recognizability, robustness, scalability, self-regulation, etc., an immune feedback control mechanism will be utilized herein for online adaptive regulation and tuning of the three parameters of PID-$K_p$, $T_i$ and $T_d$, to improve the adaptability and control effect of the control system.

Immunity is a self-physiological protection mechanism for the body to recognize, activate, differentiate and clear viruses, bacteria, foreign invading alien substances and mutated cells, and so on, and mainly uses antibodies on B cells in lymphocytes that play a leading role to recognize and clear antigens by combining with invading antigens, while TH cells and TS cells, differentiated from T cells in lymphocytes after the T cells receive an antigen invading message, stimulate and suppress generation and immune response of the B cells, respectively. As antigen increases, there is a rapid increase in TH cells and a decrease in TS cells; as the antigen is progressively reduced, there are fewer TH cells and increased TS cells and production TH cells are suppressed, and the B cells will also be reduced so that the immune feedback system gradually restores balance, to achieve the purpose of protecting the body's functional stability and well-being.

Reference to the immune feedback regulation mechanism, $K_p$, $T_i$ and $T_d$ of PID are regulated and tuned:

In N generation, there is an invasion of Ag (n) antigen, and the number of TH cells and TS cells generated by stimulation is TH (n) and TS (n) respectively, the TH cells and TS cells jointly stimulate the generation and immune response of B cells, and the total number of stimuli received by the B cells is $B(n)=TH(n)-TS(n)$ Where $$TH(n) = k_1 Ag(n),\ TS(n) = k_2 Ag(n) f(\Delta Ag(n)) = \frac{k_2 Ag(n)}{1 - e^{-\Delta Ag(n)}}$$

(it indicates that antigen increases, then TS decreases and B cells increase);

Deviations e (n) as input of the control system can also be seen as "stimulation" of the system, which is similar to the effect of the antigen on the immune system, therefore e(n) can be equal to the number of antigens Ag (n); $u_c(n)$ as the output of the control system may then correspond to stimulation of B cells by the immune system under antigen invasion, in the sense, $u_c(n)$ may also be equal to the total stimulated number B (n) of B cells; thus, there can be a regulator with feedback mechanism and variable parameters as follow:

$u_c(n)=B(n)=TH(n)-TS(n)=k_1 Ag(n)-k_2 Ag(n)$
$f(\Delta Ag(n))=(k_1-k_2 f(\Delta e(n)))e(n)$ where $$f(\Delta Ag(n)) = \frac{1}{1 - e^{-\Delta Ag(n)}},$$

when $\delta = k_2/k_1$, then $u_c(n) = (k_1 - k_2 f(\Delta e(n)))e(n) = k_1(1 - \delta * f(\Delta e(n)))e(n) = k_\mu(1 - \delta * f(\Delta e(n)))e(n)$;

The above equation is compared with the difference equation of PID, then $K_p$, $T_i$ and $T_d$ of PID can be adjusted as follows, respectively:

$$K_p = k_{\mu p}(1 - \delta_p * f(\Delta e_p(n))); T_i = k_{\mu i}(1 - \delta_i * f(\Delta e_i(n))); T_d = k_{\mu d}(1 - \delta_d * f(\Delta e_d(n))).$$

For ultra-short feedback algorithms, there is an ultra-short feedback closed loop of hypothalamus→pituitary→thyroid secreting hormone concentration in the neuroendocrine system, to suppress its own secretory activity of the neuroendocrine system, to rapidly and stably regulate and compensate for glandular secretory activity, enabling the system to have higher adaptive capacity and stability. This mechanism is exploited herein to improve fast adaptability and stability of the system, a change rate of an output u(n) of the PID controller over a sampling period $T_s$ is taken as an input of an ultra-short feedback unit, and the Hill function principle is used to generate a modified adjustment signal, then the ultra-short feedback algorithm is as follows:

$$f(\Delta u_c(n), e(n)) = \alpha\left(\frac{|\Delta u_c(n)|^m}{\lambda + |\Delta u_c(n)|^m} + \beta\right) * L_1 * L_2 = \alpha\frac{|\Delta u_c(n)|^m}{\lambda + |\Delta u_c(n)|^m} * \left(\frac{\Delta e(n)}{|\Delta e(n)|} * \frac{e(n)}{|e(n)|}\right) * \frac{\Delta u_c(n)}{|\Delta u_c(n)|}$$

Where an amplitude adjusting parameter $\alpha \in (0,1)$ can be set piecewise according to the actual interference degree of system operation under operation, $\beta \in (0,1)$ is an adjustment factor coefficient, $\Delta \in [0,1]$ is a threshold (moderately reducing a fine-tuning overshoot, the factor coefficient can take some smaller value), m (m≥1) is the Hill coefficient, $\Delta u_c(n) = u_c(n) - u_c(n-1)$ is a hormonal excitation signal.

For a control system algorithm, the algorithm is proposed by combining three algorithms of PID control algorithm, immune-evolution algorithm, ultra-short feedback algorithm, an incremental output expression of the control system algorithm obtained by combining three algorithms is:

$$\Delta u(n) = \Delta u_c(n-1) - f(\Delta u_c, e(n))$$

According to the implementation of the method described above, the pheromones produced outward by the vehicle main body based on the neural autocrine mechanism can be fully utilized at the time of regulation to select a vehicle satisfying the regulation condition, which enables close cooperation of multiple vehicle main bodies in a multi-cooperative task, sufficiently arranges a transportation capacity of each vehicle main body, and greatly improves the transport efficiency as well as the regulation precision. Meanwhile each members in the motorcade formed by the method described above in the system has high flexibility and autonomy, may adequately provoke motivation and initiative of members, so that the members can face and deal with complex problems and complex environment together, thereby solving the problem that the flexibility and autonomy of the members in conventional systems is relatively low, which is unfavorable for developing their enthusiasm and initiative to achieve the effect of 1+1>>1; and also making the motorcade have higher self-organization, robustness and reliability than those of the centralized control system.

Figure 6:
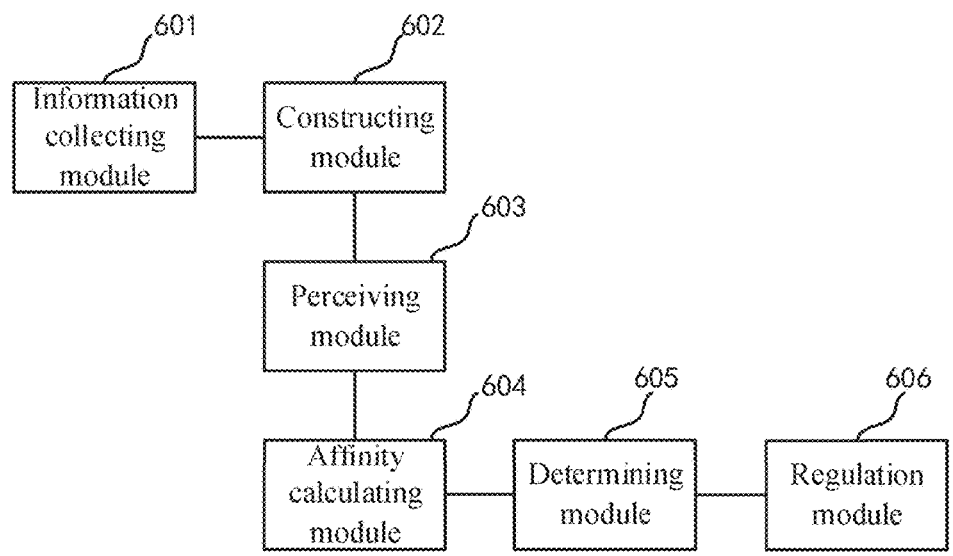
FIG. 6 is a schematic illustration of one embodiment of a neural autocrine mechanism based motorcade regulation device provided by the present invention.

The neural autocrine mechanism based motorcade regulation method in embodiments of the invention is described above, a neural autocrine mechanism based motorcade regulation device in embodiments of the present invention is described below. Referring now to FIG. 6, an embodiment of the neural autocrine mechanism based motorcade regulation device in accordance with embodiments of the invention includes:

an information collecting module 601, configured to determine a cluster position, a target position, and at least one first vehicle main body of a motorcade according to a multi-cooperative task and plan a moving path for each first vehicle main body to move to the cluster position;

a constructing module 602, configured to construct a diffusion region of a pheromone of each first vehicle main body by taking each first vehicle main body as a center, and generate a first pheromone set within the diffusion region based on the neural autocrine mechanism, wherein the first pheromone set comprises at least one first pheromone;

a perceiving module 603, configured to, during a moving process of each first vehicle main body on corresponding moving path thereof towards the cluster position, perceive in real time whether a second pheromone set transmitted by a second vehicle main body entering the diffusion region satisfies a preset proximity condition, via the first pheromone set, wherein the second pheromone set includes at least one second pheromone;

an affinity calculating module 604, configured to determine an affinity between the first pheromone set and the second pheromone set according to the first pheromone set and the second pheromone set when the second vehicle main body satisfying the proximity condition is perceived;

a determining module 605, configured to determine whether the affinity satisfies a preset regulation condition; and a regulation module 606, configured to, upon determining that the regulation condition is satisfied, acquire a movement parameter of each of the first vehicle main body and the second vehicle main body, arrange a formation for the first vehicle main body and the second vehicle main body according to the movement parameters, with which the first vehicle main body and the second vehicle main body continue to move towards the cluster position; and upon arrival of all of the first vehicle main body and the second vehicle main body at the cluster position, re-arrange the formation for all of the first vehicle main body and the second vehicle main body according to the movement parameters and make the re-arranged formation move towards the target position.

For the device according to the present embodiment, the construction and control of the motorcade are achieved through the above device, the pheromones produced outward by the vehicle main body based on the neural autocrine mechanism can be fully utilized to select a vehicle satisfying the regulation condition, which enables close cooperation of multiple vehicle main bodies in the multi-cooperative task, sufficiently arranges a transportation capacity of each vehicle main body, and greatly improves the transport efficiency as well as the regulation precision.

Figure 7:
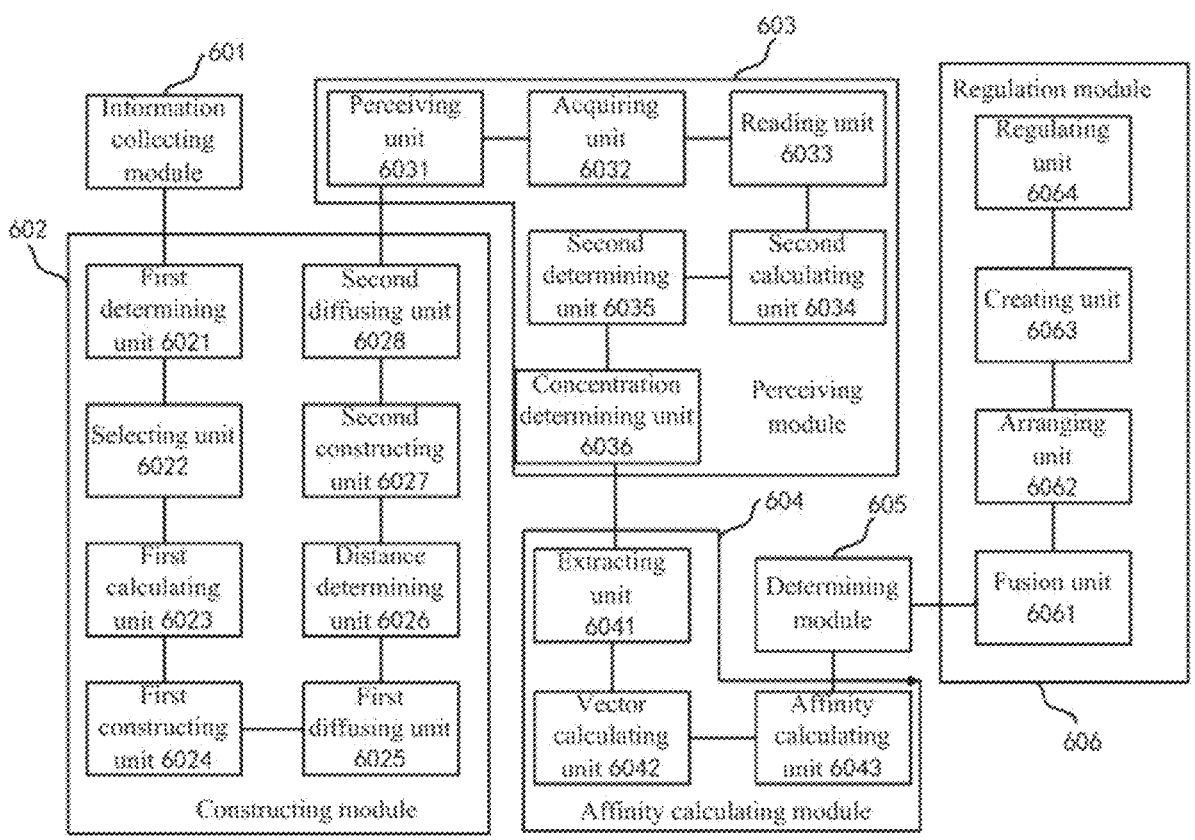
FIG. 7 is a schematic illustration of another embodiment of a neural autocrine mechanism based motorcade regulation device provided by the present invention.

Furthermore, referring to FIG. 7, which is detailed schematic diagram of each module of the neural autocrine mechanism based motorcade regulation device.

In another embodiment of the present embodiment, the constructing module includes: 602 includes:

a first determining unit 6021, configured to determine whether each first vehicle main body has a pre-cooperative vehicle main body;

a selecting unit 6022, configured to take the moving path as a filtering condition, and select a vehicle main body having a specific position on the moving path from the corresponding pre-cooperative vehicle main bodies, when there is the pre-cooperative vehicle main body is determined, to obtain a pre-cooperative vehicle main body set;

a first calculating unit 6023, configured to determine a real-time position of the first vehicle main body and calculate an information transmission direction of the first vehicle main body and each pre-cooperative vehicle main body in the corresponding pre-cooperative vehicle main body set based on the real-time position a first constructing unit 6024, configured to take the first vehicle main body as a transmission starting point and construct a directional diffusion region of the pheromone of the first vehicle main body in the information transmission direction; and a first diffusing unit 6025, configured to invoke the neural autocrine mechanism to drive the first vehicle main body to produce the first pheromone set within the directional diffusion region, and configure the first pheromone set to transmit directionally within the directional diffusion region in accordance with the information transmission direction.

In another embodiment of this embodiment, the constructing module 602 further includes:

a distance determining unit 6026, configured to determine a maximum information transmission distance of the first vehicle main body when no pre-cooperative vehicle main body is determined for each first vehicle main body;

a second constructing unit 6027, configured to take the maximum information transmission distance as a radius and construct a surrounding diffusion region of the pheromone of the first vehicle main body; and a second diffusing unit 6028, configured to invoke the neural autocrine mechanism to drive the first vehicle main body to produce the first pheromone set within the surrounding diffusion region, and configure a transmission direction of the first pheromone set to be omni-directional, to transmit the first pheromone set simultaneously in multiple directions within the surrounding diffusion region.

In another embodiment of this embodiment, the perceiving module 603 includes:

a perceiving unit 6031, configured to perceive whether a new vehicle main body enters the diffusion region via each first pheromone in the first pheromone set;

an acquiring unit 6032, configured to, when the new vehicle main body enters the diffusion region, acquire a second pheromone set, a intention and a target, which are transmitted by the new vehicle main body within the diffusion region;

a reading unit 6033, configured to select a vehicle main body having the target and the intent the same as the multi-cooperative task, and read the second pheromone set of the selected vehicle main body, to obtain a second pheromone sequence;

a second calculating unit 6034, configured to calculate and modifying a pheromone concentration of the second pheromone sequence;

a second determining unit 6035, configured to determine whether the modified pheromone concentration of the second pheromone set is greater than the pheromone concentration of the first pheromone set; and a concentration determining unit 6036, configured to determine that the new vehicle main body is the second vehicle main body adjacent to the first vehicle main body upon determining that the modified pheromone concentration of the second pheromone set is not greater than the pheromone concentration of the first pheromone set.

In another embodiment of this embodiment, the affinity calculation module 604 includes:

an extracting unit 6041, configured to extract all informational properties of each pheromone of the first pheromone set and the second pheromone set, respectively;

a vector calculating unit 6042, configured to calculate a corresponding pheromone vector according to all informational properties of each pheromone, to obtain a first pheromone vector and a second pheromone vector; and an affinity calculating unit 6043, configured to calculate a similarity between the first pheromone set and the second pheromone set according to the first pheromone vector and the second pheromone vector, to obtain a corresponding affinity.

In another embodiment of this embodiment, the affinity calculation unit 6043 is specifically configured to:

perform a square summing for differences between every two corresponding pheromone vectors of two identical or similar pheromones in the first pheromone set and the second pheromone set, to obtain the similarity of the two identical or similar pheromones; and calculate a similarity weight for each of the pheromones according to a weight ratio of each pheromone in the multi-cooperative task, and summing the calculated similarity weights to obtain an affinity between the first pheromone set and the second pheromone set.

In another embodiment of this embodiment, the movement parameter includes at least a movement speed, a movement acceleration, a movement direction, and a diffusion distance of the pheromone, and the regulating module 606 includes:

a fusion unit 6061 configured to perform a fusion calculation based on the movement speed, the movement acceleration, the movement direction and the diffusion distance, to obtain a dynamic performance of each first vehicle main body and each second vehicle main body;

an arranging unit 6062, configured to according to the dynamic performance, arrange all of the first vehicle main body and the second vehicle main body in accordance with a preset formation strategy to obtain a cooperative formation;

a creating unit 6063, configured to create a motorcade self-regulating feedback mechanism based on the cooperative formation, wherein the motorcade self-regulating feedback mechanism is used to monitor a dynamic balance of all movement parameters of each first vehicle main body and each second vehicle main body in the cooperative formation; and a regulating unit 6064, configured to control all of the first vehicle main body and the second vehicle main body, maintain a moving queue in accordance with the cooperative formation, and make real-time monitoring adjustment to each vehicle main body in the queue with the motorcade self-regulating feedback mechanism, to achieve movement to the target location, wherein the real-time monitoring adjustment includes: capturing a real-time dynamic performance of the first vehicle main body or the second vehicle main body in the cooperative formation based on the motorcade self-regulating feedback mechanism, determining whether the real-time dynamic performance satisfies a balance coefficient of the cooperative formation, and when not, controlling the corresponding vehicle main body to adjust the dynamic performance thereof, and notifying the other vehicle main body to make a cooperation adjustment.

By implementation of the above device, depending on whether the respective intended targets are consistent or close to those of other vehicle main body, whether their own resources, dynamic capabilities, and work status match a cooperation request made by a counterparty (the higher the affinity, the greater the likelihood of cooperation), and whether benefit thus obtained is in accordance with its own expectation, whether to establish a partnership is determined, thereby spontaneously and autonomously forming an interest body, such interest body may dynamically form interests ensembles/systems/leagues or add and subtract members or dismissals, to flexibly and quickly response to the variety, fast variability and high uncertainty and complexity of external environments, based on the decentralized and autonomous control mechanism of each main body, the self-organization, robustness and reliability of the system are higher than those of the centralized control system.

In the above, FIG. 6 and FIG. 7 describe in detail the neural autocrine mechanism based motorcade regulation device in the embodiment of the present invention from the perspective of modular functional entities, and an electronic equipment in the embodiment of the present invention is described below from the perspective of hardware processing.

Figure 8:
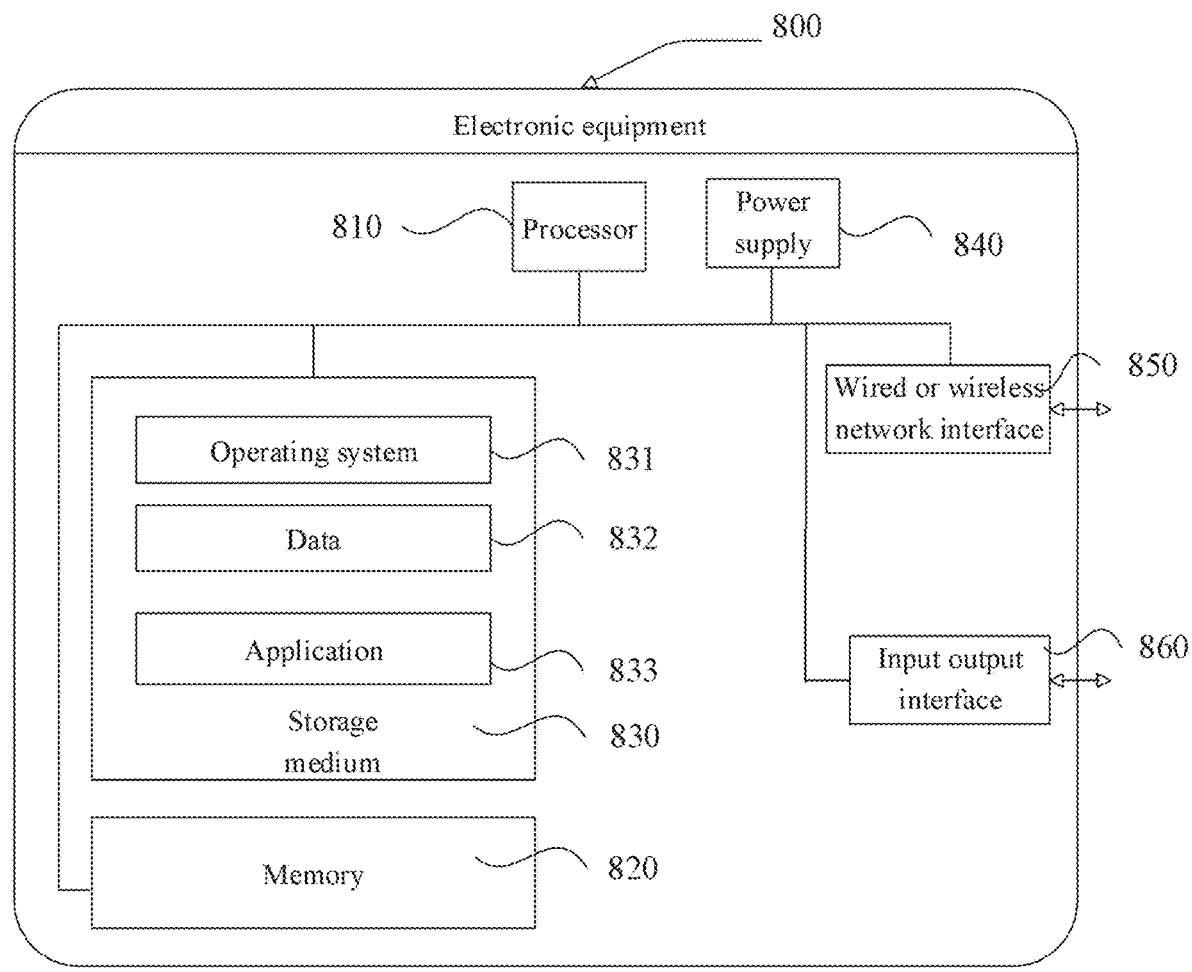
FIG. 8 is a schematic illustration of one embodiment of an electronic equipment provided by the present disclosure.

FIG. 8 is a schematic configuration diagram of an electronic equipment according to an embodiment of the present invention. The electronic equipment 800 may vary considerably due to different configurations or capabilities, and may include one or more processors (central processing units, CPU) 810 (for example, one or more processors) and memories 820, one or more storage medias 830 (e.g., one or more mass storage devices) that store applications 833 or data 832. Wherein the memory 820 and the storage medium 830 may be brief or persistent storage. The program stored in the storage medium 830 may include one or more modules (not shown), each of which may include a series of instructions operating on the electronic equipment 800. Still further, the processor 810 may be configured to communicate with the storage medium 830 to execute a series of instruction operations on the electronic equipment 800. In a practical application, this application 833 may be segmented into the functions of the information collecting module 601, the constructing module 602, the perceiving module 603, the affinity calculating module 604, the determining module 605 and the regulation module 606 (modules in a virtual device).

The electronic equipment 800 may also include one or more power supplies 840, one or more wired or wireless network interfaces 850, one or more input output interfaces 860, and/or one or more operating systems 831, such as WindowsServe, MacOSX, Unix, Linux, FreeBSD, and/or the like. One skilled in the art will appreciate that the electronic equipment structure shown in FIG. 8 may also include more or fewer components than illustrated, or combine certain components, or have a different arrangement of components.

Embodiments of the invention also provide a computer readable storage medium. The computer readable storage medium may be a non-volatile computer readable storage medium. The computer readable storage medium may also be a volatile computer readable storage medium. The computer readable storage medium has stored therein instructions or a computer program which, when executed, causes a computer to perform the steps of the neural autocrine mechanism based motorcade regulation method provided by the above embodiments.

Those skilled in the art will clearly appreciate that, for convenience and conciseness of description, specific working processes of the above described systems or devices or units, may refer to corresponding processes in the foregoing method embodiments, which are not repeated here.

An integrated unit, when implemented in the form of a software functional unit and sold or used as a stand-alone product, may be stored in one computer readable storage medium. Based on such understanding, the technical solutions of the present invention essentially, or the part contributing to the prior art, or all or a part of the technical solutions, may be implemented in a form of a software product. The computer software product is stored on a storage medium and comprises instructions for causing a computer device (which could be a personal computer, a server, a network device, or the like), to perform all or part of the steps of the methods according to the various embodiments of the present invention. While the storage media discussed above includes a variety of media in which program code can be stored, such as a USB flash drive, a removable hard disk, a read-only memory (ROM, Read-Only Memory), a random access memory (RAM, Random Access Memory), a magnetic disk, or an optical disc.

As described above, the above embodiments are merely illustrative of the technical solutions of the present invention, but are not intended to limit the present invention; Although the present invention has been described in detail with reference to the foregoing embodiments, it will be understood by those skilled in the art that the technical solutions described in the foregoing embodiments may be modified or some technical features may be replaced equivalently; those modifications or replacements will not make the essence of the corresponding technical solutions depart from the spirit and scope of the technical solutions of the embodiments of the present invention.

What is claimed is:

1. A neural autocrine mechanism based motorcade regulation method, wherein the motorcade regulation method comprises following steps:

determining a cluster position, a target position, and at least one first vehicle main body of a motorcade according to a multi-cooperative task and planning a moving path for each first vehicle main body to move to the cluster position;

constructing a diffusion region of a pheromone of each first vehicle main body by taking each first vehicle main body as a center, and generating a first pheromone set within the diffusion region based on the neural autocrine mechanism, wherein the first pheromone set comprises at least one first pheromone;

during a moving process of each first vehicle main body on a corresponding moving path thereof towards the cluster position, perceiving in real time, whether a second pheromone set transmitted by a second vehicle main body entering the diffusion region satisfies a preset proximity condition, via the first pheromone set, wherein the second pheromone set comprises at least one second pheromone;

when the proximity condition is satisfied, determining an affinity between the first pheromone set and the second pheromone set according to the first pheromone set and the second pheromone set;

determining whether the affinity satisfies a preset regulation condition;

when the regulation condition is satisfied, acquiring a movement parameter of each of the first vehicle main body and the second vehicle main body, arranging a formation for the first vehicle main body and the second vehicle main body according to the movement parameters, with which the first vehicle main body and the second vehicle main body continue to move towards the cluster position; and upon arrival of all of the first vehicle main body and the second vehicle main body at the cluster position, re-arranging the formation for all of the first vehicle main body and the second vehicle main body according to the movement parameters with which the first vehicle main body and the second vehicle main body move towards the target position.

2. The neural autocrine mechanism based motorcade regulation method according to claim 1, wherein the step of determining a cluster position, a target position, and at least one first vehicle main body of a motorcade and planning a moving path for each of the first vehicle main bodies to move to the cluster position, according to a multi-cooperative task comprises following steps:

determining whether each first vehicle main body has a pre-cooperative vehicle main body;

when yes, taking the moving path as a filtering condition, and selecting a vehicle main body having a specific position on the moving path from the corresponding pre-cooperative vehicle main bodies, to obtain a pre-cooperative vehicle main body set;

determining a real-time position of the first vehicle main body and calculating an information transmission direction of the first vehicle main body and each pre-cooperative vehicle main body in the corresponding pre-cooperative vehicle main body set based on the real-time position;

taking the first vehicle main body as a transmission starting point and constructing a directional diffusion region of the pheromone of the first vehicle main body in the information transmission direction; and invoking the neural autocrine mechanism to drive the first vehicle main body to produce the first pheromone set within the directional diffusion region, and configuring the first pheromone set to transmit directionally within the directional diffusion region in accordance with the information transmission direction.

3. The neural autocrine mechanism based motorcade regulation method according to claim 2, wherein the step of determining a cluster position, a target position, and at least one first vehicle main body of a motorcade and planning a moving path for each of the first vehicle main bodies to move to the cluster position, according to a multi-cooperative task further comprises following steps:

determining a maximum information transmission distance of the first vehicle main body when no pre-cooperative vehicle main body is determined for each first vehicle main body;

taking the maximum information transmission distance as a radius and constructing a surrounding diffusion region of the pheromone of the first vehicle main body; and invoking the neural autocrine mechanism to drive the first vehicle main body to produce the first pheromone set within the surrounding diffusion region, and configuring a transmission direction of the first pheromone set to be omni-directional, to transmit the first pheromone set simultaneously in multiple directions within the surrounding diffusion region.

4. The neural autocrine mechanism based motorcade regulation method according to claim 1, wherein the step of perceiving in real time, whether a second pheromone set transmitted by a second vehicle main body entering the diffusion region satisfies a preset proximity condition, via the first pheromone set comprises following steps:

perceiving whether a new vehicle main body enters the diffusion region via each first pheromone in the first pheromone set;

when the new vehicle main body enters the diffusion region, acquiring a second pheromone set, an intention and a target, which are transmitted by the new vehicle main body within the diffusion region;

selecting a vehicle main body having the same target and the intent as the multi-cooperative task, and reading the second pheromone set of the selected vehicle main body, to obtain a second pheromone sequence;

calculating and modifying a pheromone concentration of the second pheromone sequence;

determining whether the modified pheromone concentration of the second pheromone set is greater than the pheromone concentration of the first pheromone set; and when not, determining that the new vehicle main body is the second vehicle main body adjacent to the first vehicle main body.

5. The neural autocrine mechanism based motorcade regulation method according to claim 1, wherein the step of determining an affinity between the first pheromone set and the second pheromone set according to the first pheromone set and the second pheromone set comprises following steps:

extracting all informational properties of each pheromone of the first pheromone set and the second pheromone set, respectively;

calculating a corresponding pheromone vector according to all informational properties of each pheromone, to obtain a first pheromone vector and a second pheromone vector; and calculating a similarity between the first pheromone set and the second pheromone set according to the first pheromone vector and the second pheromone vector, to obtain a corresponding affinity.

6. The neural autocrine mechanism based motorcade regulation method according to claim 5, wherein the step of calculating a similarity between the first pheromone set and the second pheromone set according to the first pheromone vector and the second pheromone vector, to obtain a corresponding affinity comprises following steps:

performing a square summing for differences between every two corresponding pheromone vectors of two identical or similar pheromones in the first pheromone set and the second pheromone set, to obtain the similarity of the two identical or similar pheromones; and calculating a similarity weight for each of the pheromones according to a weight ratio of each pheromone in the multi-cooperative task, and summing the calculated similarity weights to obtain an affinity between the first pheromone set and the second pheromone set.

7. The neural autocrine mechanism based motorcade regulation method according to claim 1, wherein the movement parameter comprises at least a movement speed, a movement acceleration, a movement direction, and a diffusion distance of the pheromone, and wherein the step of re-arranging the formation for all of the first vehicle main body and the second vehicle main body according to the movement parameters with which the first vehicle main body and the second vehicle main body move towards the target position comprises following steps:

performing a fusion calculation based on the movement speed, the movement acceleration, the movement direction and the diffusion distance, to obtain a dynamic performance of each first vehicle main body and each second vehicle main body;

according to the dynamic performance, arranging all of the first vehicle main body and the second vehicle main body in accordance with a preset formation strategy to obtain a cooperative formation;

creating a motorcade self-regulating feedback mechanism based on the cooperative formation, wherein the motorcade self-regulating feedback mechanism is used to monitor a dynamic balance of all movement parameters of each first vehicle main body and each second vehicle main body in the cooperative formation; and controlling all of the first vehicle main body and the second vehicle main body, maintaining a moving queue in accordance with the cooperative formation, and making real-time monitoring adjustment to each vehicle main body in the queue with the motorcade self-regulating feedback mechanism, to achieve movement to the target location, wherein the real-time monitoring adjustment comprises: capturing a real-time dynamic performance of the first vehicle main body or the second vehicle main body in the cooperative formation based on the motorcade self-regulating feedback mechanism, determining whether the real-time dynamic performance satisfies a balance coefficient of the cooperative formation, and when not, controlling the corresponding vehicle main body to adjust the dynamic performance thereof, and notifying the other vehicle main body to make a cooperation adjustment.

8. A neural autocrine mechanism based motorcade regulation device, wherein the motorcade regulation device comprises:

an information collecting module, configured to determine a cluster position, a target position, and at least one first vehicle main body of a motorcade according to a multi-cooperative task and plan a moving path for each first vehicle main body to move to the cluster position;

a constructing module, configured to construct a diffusion region of a pheromone of each first vehicle main body by taking each first vehicle main body as a center, and generate a first pheromone set within the diffusion region based on the neural autocrine mechanism, wherein the first pheromone set comprises at least one first pheromone;

a perceiving module, configured to, during a moving process of each first vehicle main body on corresponding moving path thereof towards the cluster position, perceive in real time whether a second pheromone set transmitted by a second vehicle main body entering the diffusion region satisfies a preset proximity condition, via the first pheromone set, wherein the second pheromone set comprises at least one second pheromone;

an affinity calculating module, configured to determine an affinity between the first pheromone set and the second pheromone set according to the first pheromone set and the second pheromone set when the second vehicle main body satisfying the proximity condition is perceived;

a determining module, configured to determine whether the affinity satisfies a preset regulation condition; and a regulation module, configured to, upon determining that the regulation condition is satisfied, acquire a movement parameter of each of the first vehicle main body and the second vehicle main body, arrange a formation for the first vehicle main body and the second vehicle main body according to the movement parameters, with which the first vehicle main body and the second vehicle main body continue to move towards the cluster position; and upon arrival of all of the first vehicle main body and the second vehicle main body at the cluster position, re-arrange the formation for all of the first vehicle main body and the second vehicle main body according to the movement parameters and make the re-arranged formation move towards the target position.

9. An electronic equipment comprising a memory, a processor, and a computer program stored in the memory and executable on the processor, wherein when executed by the processor, the computer program implements the steps of the neural autocrine mechanism based motorcade regulation method according to claim 1.

10. The electronic equipment according to claim 9, wherein the step of determining a cluster position, a target position, and at least one first vehicle main body of a motorcade and planning a moving path for each of the first vehicle main bodies to move to the cluster position, according to a multi-cooperative task comprises following steps:

determining whether each first vehicle main body has a pre-cooperative vehicle main body;

when yes, taking the moving path as a filtering condition, and selecting a vehicle main body having a specific position on the moving path from the corresponding pre-cooperative vehicle main bodies, to obtain a pre-cooperative vehicle main body set;

determining a real-time position of the first vehicle main body and calculating an information transmission direction of the first vehicle main body and each pre-cooperative vehicle main body in the corresponding pre-cooperative vehicle main body set based on the real-time position;

taking the first vehicle main body as a transmission starting point and constructing a directional diffusion region of the pheromone of the first vehicle main body in the information transmission direction; and invoking the neural autocrine mechanism to drive the first vehicle main body to produce the first pheromone set within the directional diffusion region, and configuring the first pheromone set to transmit directionally within the directional diffusion region in accordance with the information transmission direction.

11. The electronic equipment according to claim 10, wherein the step of determining a cluster position, a target position, and at least one first vehicle main body of a motorcade and planning a moving path for each of the first vehicle main bodies to move to the cluster position, according to a multi-cooperative task further comprises following steps:

determining a maximum information transmission distance of the first vehicle main body when no pre-cooperative vehicle main body is determined for each first vehicle main body;

taking the maximum information transmission distance as a radius and constructing a surrounding diffusion region of the pheromone of the first vehicle main body; and invoking the neural autocrine mechanism to drive the first vehicle main body to produce the first pheromone set within the surrounding diffusion region, and configuring a transmission direction of the first pheromone set to be omni-directional, to transmit the first pheromone set simultaneously in multiple directions within the surrounding diffusion region.

12. The electronic equipment according to claim 9, wherein the step of perceiving in real time, whether a second pheromone set transmitted by a second vehicle main body entering the diffusion region satisfies a preset proximity condition, via the first pheromone set comprises following steps:
- perceiving whether a new vehicle main body enters the diffusion region via each first pheromone in the first pheromone set;
- when the new vehicle main body enters the diffusion region, acquiring a second pheromone set, an intention and a target, which are transmitted by the new vehicle main body within the diffusion region;
- selecting a vehicle main body having the same target and the intent as the multi-cooperative task, and reading the second pheromone set of the selected vehicle main body, to obtain a second pheromone sequence;
- calculating and modifying a pheromone concentration of the second pheromone sequence;
- determining whether the modified pheromone concentration of the second pheromone set is greater than the pheromone concentration of the first pheromone set; and
- when not, determining that the new vehicle main body is the second vehicle main body adjacent to the first vehicle main body.

13. The electronic equipment according to claim 9, wherein the step of determining an affinity between the first pheromone set and the second pheromone set according to the first pheromone set and the second pheromone set comprises following steps:
- extracting all informational properties of each pheromone of the first pheromone set and the second pheromone set, respectively;
- calculating a corresponding pheromone vector according to all informational properties of each pheromone, to obtain a first pheromone vector and a second pheromone vector; and
- calculating a similarity between the first pheromone set and the second pheromone set according to the first pheromone vector and the second pheromone vector, to obtain a corresponding affinity; and
- wherein the step of calculating a similarity between the first pheromone set and the second pheromone set according to the first pheromone vector and the second pheromone vector, to obtain a corresponding affinity comprises following steps:
- performing a square summing for differences between every two corresponding pheromone vectors of two identical or similar pheromones in the first pheromone set and the second pheromone set, to obtain the similarity of the two identical or similar pheromones; and
- calculating a similarity weight for each of the pheromones according to a weight ratio of each pheromone in the multi-cooperative task, and summing the calculated similarity weights to obtain an affinity between the first pheromone set and the second pheromone set.

14. The electronic equipment according to claim 9, wherein the movement parameter comprises at least a movement speed, a movement acceleration, a movement direction, and a diffusion distance of the pheromone, and wherein the step of re-arranging the formation for all of the first vehicle main body and the second vehicle main body according to the movement parameters with which the first vehicle main body and the second vehicle main body move towards the target position comprises following steps:
- performing a fusion calculation based on the movement speed, the movement acceleration, the movement direction and the diffusion distance, to obtain a dynamic performance of each first vehicle main body and each second vehicle main body;
- according to the dynamic performance, arranging all of the first vehicle main body and the second vehicle main body in accordance with a preset formation strategy to obtain a cooperative formation;
- creating a motorcade self-regulating feedback mechanism based on the cooperative formation, wherein the motorcade self-regulating feedback mechanism is used to monitor a dynamic balance of all movement parameters of each first vehicle main body and each second vehicle main body in the cooperative formation; and
- controlling all of the first vehicle main body and the second vehicle main body, maintaining a moving queue in accordance with the cooperative formation, and making real-time monitoring adjustment to each vehicle main body in the queue with the motorcade self-regulating feedback mechanism, to achieve movement to the target location, wherein the real-time monitoring adjustment comprises: capturing a real-time dynamic performance of the first vehicle main body or the second vehicle main body in the cooperative formation based on the motorcade self-regulating feedback mechanism, determining whether the real-time dynamic performance satisfies a balance coefficient of the cooperative formation, and when not, controlling the corresponding vehicle main body to adjust the dynamic performance thereof, and notifying the other vehicle main body to make a cooperation adjustment.

15. A non-transitory computer-readable storage medium storing a computer program, wherein when executed by a processor, the computer program implements the steps of the neural autocrine mechanism based motorcade regulation method according to claim 1.

16. The non-transitory computer-readable storage medium storing a computer program according to claim 15, wherein the step of determining a cluster position, a target position, and at least one first vehicle main body of a motorcade and planning a moving path for each of the first vehicle main bodies to move to the cluster position, according to a multi-cooperative task comprises following steps:
- determining whether each first vehicle main body has a pre-cooperative vehicle main body;
- when yes, taking the moving path as a filtering condition, and selecting a vehicle main body having a specific position on the moving path from the corresponding pre-cooperative vehicle main bodies, to obtain a pre-cooperative vehicle main body set;
- determining a real-time position of the first vehicle main body and calculating an information transmission direction of the first vehicle main body and each pre-cooperative vehicle main body in the corresponding pre-cooperative vehicle main body set based on the real-time position;
- taking the first vehicle main body as a transmission starting point and constructing a directional diffusion region of the pheromone of the first vehicle main body in the information transmission direction; and
- invoking the neural autocrine mechanism to drive the first vehicle main body to produce the first pheromone set within the directional diffusion region, and configuring the first pheromone set to transmit directionally within the directional diffusion region in accordance with the information transmission direction.

17. The non-transitory computer-readable storage medium storing a computer program according to claim 16, wherein the step of determining a cluster position, a target position, and at least one first vehicle main body of a motorcade and planning a moving path for each of the first vehicle main bodies to move to the cluster position, according to a multi-cooperative task further comprises following steps:
   determining a maximum information transmission distance of the first vehicle main body when no pre-cooperative vehicle main body is determined for each first vehicle main body;
   taking the maximum information transmission distance as a radius and constructing a surrounding diffusion region of the pheromone of the first vehicle main body; and
   invoking the neural autocrine mechanism to drive the first vehicle main body to produce the first pheromone set within the surrounding diffusion region, and configuring a transmission direction of the first pheromone set to be omni-directional, to transmit the first pheromone set simultaneously in multiple directions within the surrounding diffusion region.

18. The non-transitory computer-readable storage medium storing a computer program according to claim 15, wherein the step of perceiving in real time, whether a second pheromone set transmitted by a second vehicle main body entering the diffusion region satisfies a preset proximity condition, via the first pheromone set comprises following steps:
   perceiving whether a new vehicle main body enters the diffusion region via each first pheromone in the first pheromone set;
   when the new vehicle main body enters the diffusion region, acquiring a second pheromone set, an intention and a target, which are transmitted by the new vehicle main body within the diffusion region;
   selecting a vehicle main body having the same target and the intent as the multi-cooperative task, and reading the second pheromone set of the selected vehicle main body, to obtain a second pheromone sequence;
   calculating and modifying a pheromone concentration of the second pheromone sequence;
   determining whether the modified pheromone concentration of the second pheromone set is greater than the pheromone concentration of the first pheromone set; and
   when not, determining that the new vehicle main body is the second vehicle main body adjacent to the first vehicle main body.

19. The non-transitory computer-readable storage medium storing a computer program according to claim 15, wherein the step of determining an affinity between the first pheromone set and the second pheromone set according to the first pheromone set and the second pheromone set comprises following steps:
   extracting all informational properties of each pheromone of the first pheromone set and the second pheromone set, respectively;
   calculating a corresponding pheromone vector according to all informational properties of each pheromone, to obtain a first pheromone vector and a second pheromone vector; and
   calculating a similarity between the first pheromone set and the second pheromone set according to the first pheromone vector and the second pheromone vector, to obtain a corresponding affinity, and
   wherein the step of calculating a similarity between the first pheromone set and the second pheromone set according to the first pheromone vector and the second pheromone vector, to obtain a corresponding affinity comprises following steps:
   performing a square summing for differences between every two corresponding pheromone vectors of two identical or similar pheromones in the first pheromone set and the second pheromone set, to obtain the similarity of the two identical or similar pheromones; and
   calculating a similarity weight for each of the pheromones according to a weight ratio of each pheromone in the multi-cooperative task, and summing the calculated similarity weights to obtain an affinity between the first pheromone set and the second pheromone set.

20. The non-transitory computer-readable storage medium storing a computer program according to claim 15, wherein the movement parameter comprises at least a movement speed, a movement acceleration, a movement direction, and a diffusion distance of the pheromone, and wherein the step of re-arranging the formation for all of the first vehicle main body and the second vehicle main body according to the movement parameters with which the first vehicle main body and the second vehicle main body move towards the target position comprises following steps:
   performing a fusion calculation based on the movement speed, the movement acceleration, the movement direction and the diffusion distance, to obtain a dynamic performance of each first vehicle main body and each second vehicle main body;
   according to the dynamic performance, arranging all of the first vehicle main body and the second vehicle main body in accordance with a preset formation strategy to obtain a cooperative formation;
   creating a motorcade self-regulating feedback mechanism based on the cooperative formation, wherein the motorcade self-regulating feedback mechanism is used to monitor a dynamic balance of all movement parameters of each first vehicle main body and each second vehicle main body in the cooperative formation; and
   controlling all of the first vehicle main body and the second vehicle main body, maintaining a moving queue in accordance with the cooperative formation, and making real-time monitoring adjustment to each vehicle main body in the queue with the motorcade self-regulating feedback mechanism, to achieve movement to the target location, wherein the real-time monitoring adjustment comprises: capturing a real-time dynamic performance of the first vehicle main body or the second vehicle main body in the cooperative formation based on the motorcade self-regulating feedback mechanism, determining whether the real-time dynamic performance satisfies a balance coefficient of the cooperative formation, and when not, controlling the corresponding vehicle main body to adjust the dynamic performance thereof, and notifying the other vehicle main body to make a cooperation adjustment.

* * * * *